US011376056B2

(12) United States Patent
Rossel

(10) Patent No.: US 11,376,056 B2
(45) Date of Patent: Jul. 5, 2022

(54) PEN FOR THE TREATMENT OF DERMATOLOGICAL DISORDERS AND METHOD FOR USE THEREOF

(71) Applicant: OYSTERSHELL NV, Merelbeke (BE)

(72) Inventor: Bart Rossel, Nederzwalm (BE)

(73) Assignee: OYSTERSHELL NV, Drongen (BE)

( * ) Notice: Subject to any disclaimer, the term of this patent is extended or adjusted under 35 U.S.C. 154(b) by 61 days.

(21) Appl. No.: 15/570,522

(22) PCT Filed: May 4, 2016

(86) PCT No.: PCT/IB2016/052547
§ 371 (c)(1),
(2) Date: Oct. 30, 2017

(87) PCT Pub. No.: WO2016/178161
PCT Pub. Date: Nov. 10, 2016

(65) Prior Publication Data
US 2018/0140344 A1 May 24, 2018

(30) Foreign Application Priority Data

May 4, 2015 (BE) .................................. 2015/5283
Jun. 3, 2015 (BE) .................................. 2015/5341

(51) Int. Cl.
*A61B 18/02* (2006.01)
*A61F 7/00* (2006.01)
*A61F 7/02* (2006.01)

(52) U.S. Cl.
CPC .......... *A61B 18/0218* (2013.01); *A61B 18/02* (2013.01); *A61F 7/0053* (2013.01);
(Continued)

(58) Field of Classification Search
CPC ................ A61B 18/0218; A61B 18/02; A61B 2018/0231; A61B 2018/0262;
(Continued)

(56) References Cited

U.S. PATENT DOCUMENTS 2,746,264 A * 5/1956 Keyes .................... A61B 18/02
62/293
2,982,112 A   5/1961 Keyes
(Continued)

FOREIGN PATENT DOCUMENTS

CN      101222948 A      7/2008
CN        1093769 A     10/2014
(Continued)

OTHER PUBLICATIONS

Search Report received in Swedish Patent Application No. 1650599-2, dated May 9, 2018.

*Primary Examiner* — Thomas A Giuliani
(74) *Attorney, Agent, or Firm* — Vorys, Sater, Seymour and Pease LLP

(57) ABSTRACT

The present invention relates to a pen for the treatment of dermatological disorders, such as warts and the like, by means of a coolant. The pen includes a distal part having a holder for the storage of a coolant and a proximal part with an applicator for the administration of the coolant to the dermatological surface for treatment. These parts extend axially and are in coolant communication by means of a coolant passage in the proximal part, in which a valve body is provided for closing off and/or opening the passage. The passage is provided with at least one bypass for the coolant. In addition, the invention relates to a method for the administration of the pen.

26 Claims, 10 Drawing Sheets

(52) U.S. Cl.
CPC ........ *A61F 7/02* (2013.01); *A61F 2007/0003* (2013.01); *A61F 2007/0052* (2013.01); *A61F 2007/0068* (2013.01); *A61F 2007/0087* (2013.01)

(58) Field of Classification Search
CPC .... A61B 2018/0268; A61B 2018/0275; A61B 2018/00005; A61B 2018/00029; A61F 7/02; A61F 2007/0003; A61F 2007/0052; A61F 2007/0068; A61F 2007/0087; A61F 7/0085; A61F 2007/0063; B65D 83/44–50; F16K 15/044
USPC .............. 137/513.7; 606/20–26; 607/96, 104
See application file for complete search history.

(56) References Cited

U.S. PATENT DOCUMENTS

| | | | | |
|---|---|---|---|---|
| 3,056,423 | A * | 10/1962 | Lieser | F16K 15/044 137/493.7 |
| 5,738,682 | A * | 4/1998 | Jensma | A61B 18/0218 606/23 |
| 2008/0169047 | A1* | 7/2008 | Connolly | A61M 15/0041 141/19 |
| 2008/0221561 | A1* | 9/2008 | Geiger | A61B 18/0218 606/22 |
| 2009/0054868 | A1* | 2/2009 | Sharkey | A61B 18/04 604/515 |
| 2010/0042087 | A1* | 2/2010 | Goldboss | A61B 18/0218 606/22 |
| 2011/0040361 | A1* | 2/2011 | Levy | A61F 7/00 607/114 |
| 2011/0152850 | A1 | 6/2011 | Niedbala et al. | |
| 2013/0030385 | A1* | 1/2013 | Schultz | A61B 18/1492 604/247 |
| 2013/0103127 | A1* | 4/2013 | Muller | A61M 19/00 607/107 |
| 2014/0163456 | A1 | 6/2014 | Kiss | |
| 2015/0359664 | A1* | 12/2015 | Herweijer | A61B 18/02 604/290 |

FOREIGN PATENT DOCUMENTS

| | | |
|---|---|---|
| EP | 2468204 A1 | 6/2012 |
| FR | 2981639 A1 | 4/2013 |
| WO | WO 2004/045434 A2 | 6/2004 |
| WO | WO 2007/009282 A1 | 1/2007 |
| WO | WO 2014/114696 A1 | 7/2014 |

* cited by examiner

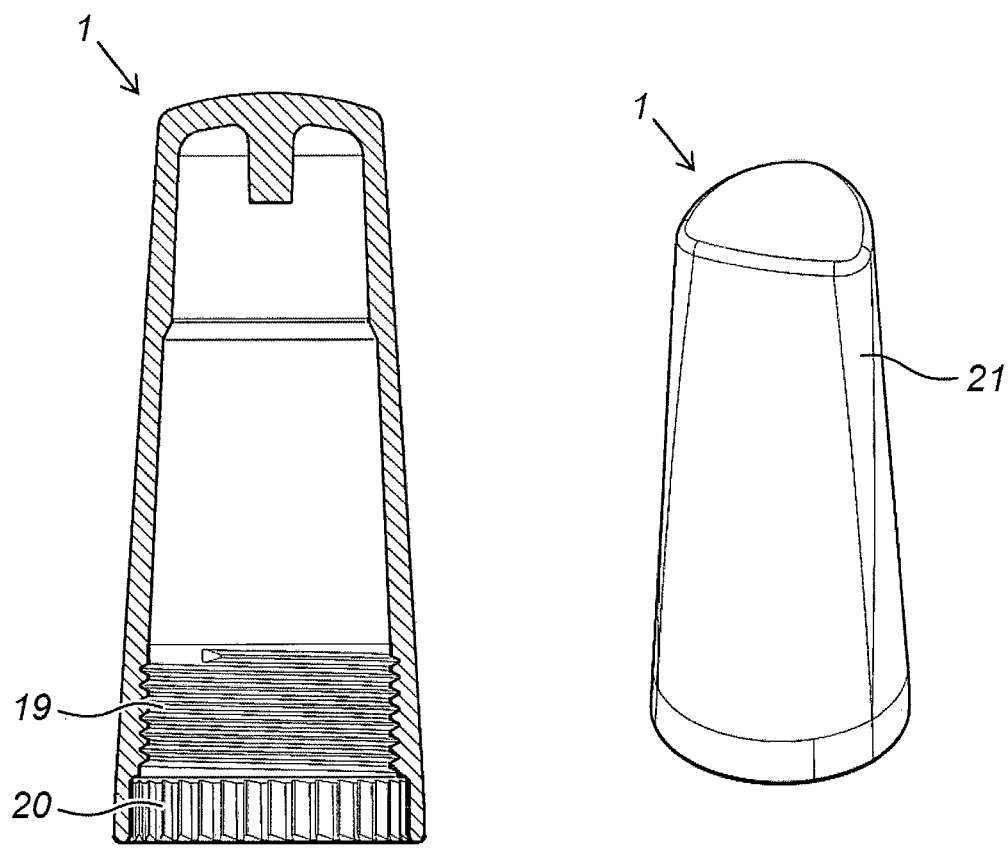
Figure 6
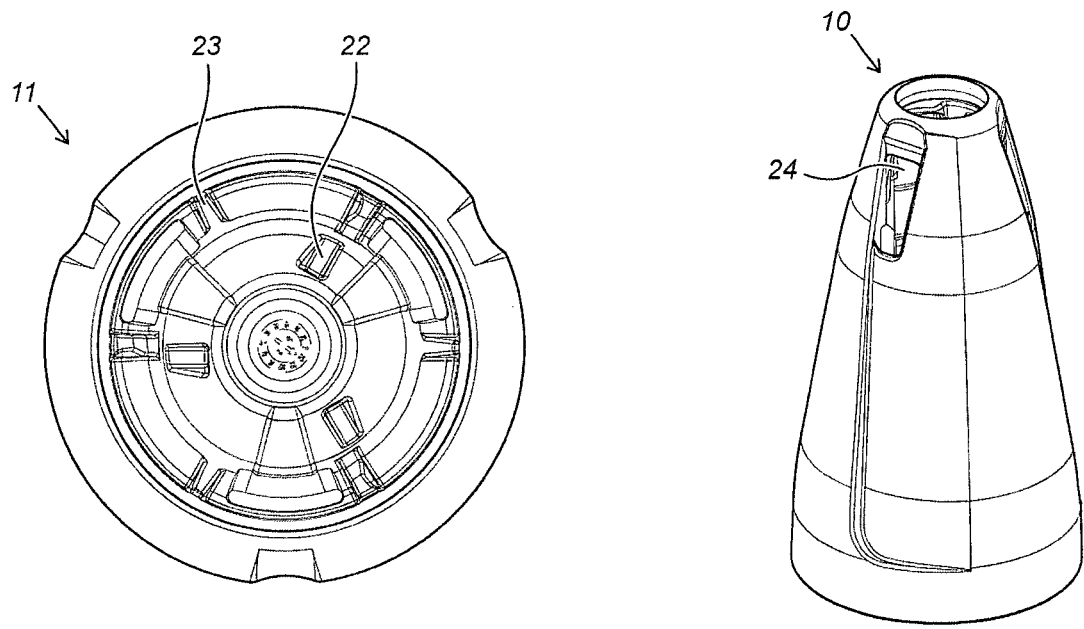
Figure 7 Figure 8

PEN FOR THE TREATMENT OF DERMATOLOGICAL DISORDERS AND METHOD FOR USE THEREOF

CROSS-REFERENCE TO RELATED APPLICATIONS

This application is the U.S. National Phase under 35. U.S.C. § 371 of International Application PCT/IB2016/052547, filed May 4, 2016, which claims priority to Belgium Patent Application No. BE2015/5283, filed May 4, 2015 and Belgium Patent Application No. BE2015/5341, filed Jun. 3, 2015. The disclosures of the above-described applications are hereby incorporated by reference in their entirety.

TECHNICAL DOMAIN

The present invention relates to a pen for the treatment of dermatological disorders and a method for use thereof. The present invention more in particular relates to a pen by which evaporative cooling can be applied to an area to treat, related to dermatological disorders, such as, for example, warts.

STATE OF THE ART

The present invention relates to a pen for the administration of evaporative cooling, in particular for use in the treatment of dermatological disorders, such as, for example, warts.

A pen for the administration of evaporative cooling appropriate for home use, has to be compact, easy and safe to use, and it has to be able to deliver efficient evaporative cooling. Moreover, it is desirable that such a pen for home use has a low cost price. It can also be desirable that such a pen for home use is a disposable pen, that can be disposed of once it has been used.

A pen for the administration of evaporative cooling is known from EP 2 468 204, under the form of a self-sustained, disposable, cryosurgical pen that can administer a cryogenic fluid, such as a flow of liquid dinitrogen oxide ($N_2O$), carbon dioxide or argon. The cryogenic fluid can either directly be applied to the area to treat, for example a wart on the skin or be delivered to an applicator that is subsequently brought in contact with the area to treat. Moreover, the pen comprises at least one filter that is placed in the flow passage and is configured for facilitating the flow of cryogenic fluid. EP 2 468 204 describes the problem that the pen cannot realize the required low temperatures during a sufficiently long time, necessary for the treatment of warts. In particular, the required low temperatures can be reached by the pen from EP 2 468 204, but not during a sufficiently long time.

EP 2 648 204 also describes the problem that the construction of the disclosed warts pens involves a relatively high cost prices of the warts pens.

The present invention aims to find a solution for of the above-mentioned problem.

The aim of the present invention is more in particular a pen for the treatment of dermatological disorders, via the administration of evaporative cooling, appropriate for home use that is compact, easy and safe to use, can deliver efficient evaporative cooling, has a low cost prices and is disposable.

SUMMARY OF THE INVENTION

An aspect of the invention relates to a pen for the treatment of dermatological disorders, such as warts, by means of a coolant, which pen comprises: a distal part comprising a holder for the storage of a coolant and a proximal part comprising an applicator for the administration of the coolant to the dermatological surface to treat, which parts extend axially and which parts are in coolant communication by means of a coolant passage in the proximal part, in which a valve body is provided for closing off and/or opening the passage, in which the passage is provided with at least one bypass for the coolant.

Via the bypass, the velocity of the coolant can be regulated.

According to an aspect of the pen, the applicator contains an administration surface and the average pore size of the applicator decreases in the axial direction to the administration surface.

Decrease of the average pore size of the applicator in the direction of the administration surface provides sufficient room for removing the gas that has been generated during evaporative cooling, resulting in an increased storage of cold.

According to an aspect of the pen, the proximal part of the pen, a closing cap or both are the proximal part of the pen and the closing cap is provided with a ventilation opening for removing a gaseous coolant.

By means of a ventilation opening, gas that is generated during the process of evaporative cooling, can escape. Because the gas can escape via a ventilation opening, the creation of overpressure in the pen can be avoided.

A second aspect of the invention relates to a method for the administration of a pen according to the present invention, which method comprises:

providing the pen for the treatment of dermatological disorders, which pen is provided with a removable closing cap;

flowing a coolant under increased pressure from the holder for the storing of the coolant to the valve body;

exercising an external pressure on the proximal part of the pen for the administration of the valve body, which external pressure is exercised in opposite direction to the pressure exercised by the coolant;

flowing the coolant past the valve body to the applicator;

realizing the evaporative cooling at the applicator;

removing the closing cap from the pen.

The exercise of an external pressure on the proximal part of the pen, in opposite direction to a pressure exercised by the coolant, will only allow a flow of coolant as long as this external pressure is maintained.

In a third aspect, the invention provides the use of a pen according to an embodiment of the invention in the treatment of warts.

Hence, to this aspect, the following method is associated. A method for the administration of a wart pen, which method comprises the following steps:

putting at disposal a wart pen appropriate for the treatment of warts, in which the cart pen comprises:

a cartridge housing 1 in which a gas cartridge 2 is placed at least temporarily, which gas cartridge 2 contains a coolant under increased pressure;

a dose-measuring device with a coolant, which dose-measuring device is appropriate for being attached at a distal side to a cartridge housing 1, which dose-measuring device is equipped at a proximal side with an applicator 7 provided with an administration surface for administrating low temperatures to one or more warts to treat, which dose-measuring device comprises distally to the applicator 7 a perforator 5 which is arranged for puncturing the gas cartridge 2 and which dose-measuring device is provided between the applicator 7 and the perforator 5 with a valve body for closing off and/or opening the coolant passage;

a closing cap 11 appropriate for being positioned in a removable manner at or being attached to the proximal side of the dose-measuring device;

administering the valve body;

optionally, using the applicator 7 at one or more warts;

at which for administering the valve body, the closing cap 11 is attached to the proximal side of the dose-measuring device, and the closing cap 11 is removed after administering the valve body.

The attachment of the closing cap 11 at the proximal side of the dose-measuring device protects the applicator 7 from the environment, so that when administering the valve body, the applicator 7 can be cooled down faster by the evaporative cooling of the coolant at the applicator 7 than when the closing cap 11 would not be attached at the proximal side of the dose-measuring device.

DESCRIPTION OF THE FIGURES

For a better understanding of the present invention, it is referred to the detailed description of the invention, by way of example, which should be read together with the following figures, in which corresponding reference numbers refer to corresponding elements:

FIG. 6 shows a cross-sectional view in the longitudinal direction of a possible embodiment of a back housing, next to a three-dimensional view of a possible embodiment of the back housing, according to the present invention.

FIG. 7 is a cross-sectional view of a possible embodiment of a closing cap according to the present invention.

FIG. 8 shows a possible embodiment of a front housing according to the present invention.

DETAILED DESCRIPTION

Figure 1:
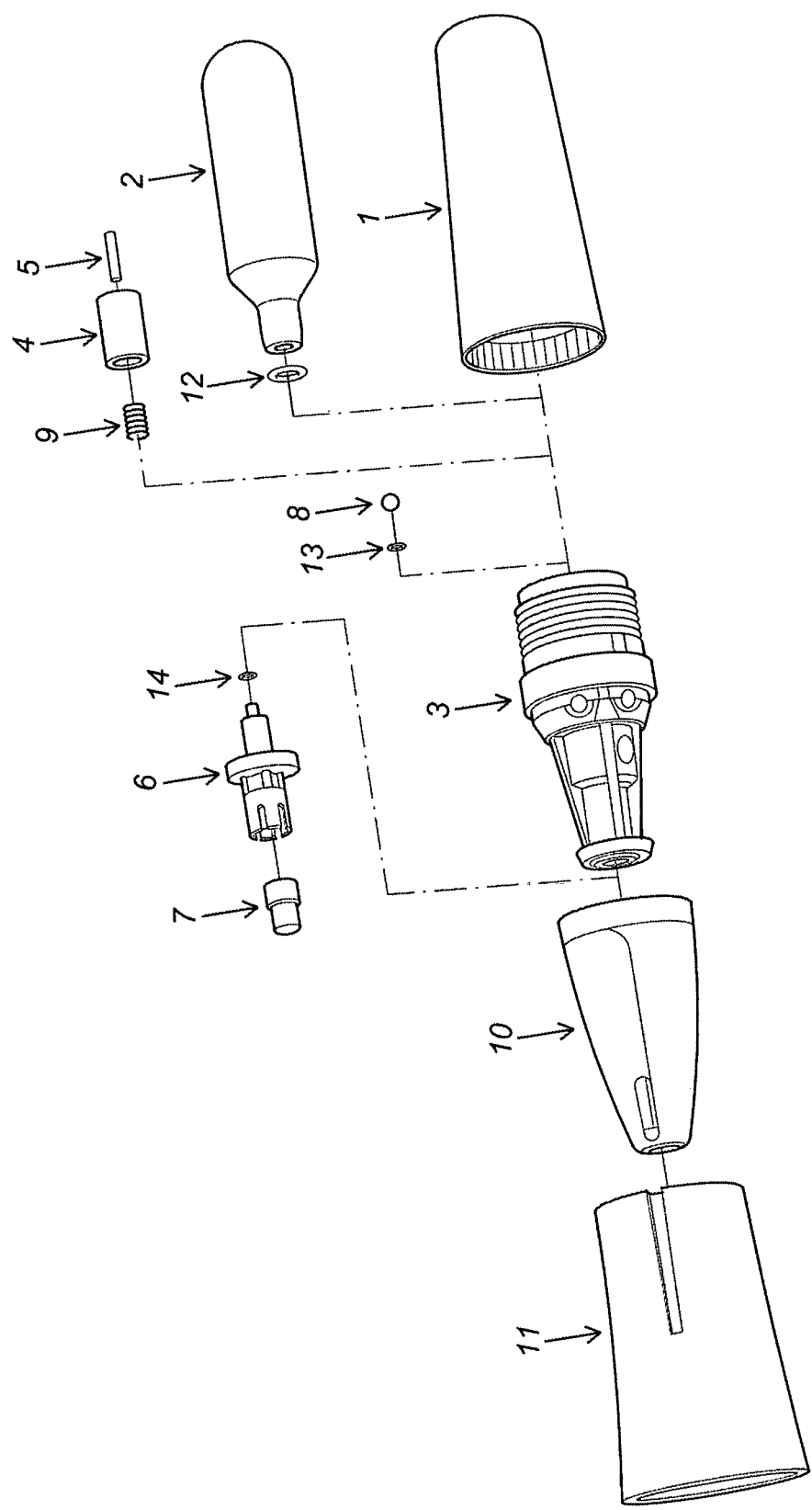
FIG. 1 is an exploded view of a possible embodiment of a pen according to the present invention.

The present invention relates to a pen for the treatment of dermatological disorders and a method for use thereof.

Unless otherwise specified, all terms used in the description of the invention, including technical and scientific terms, shall have the meaning as they are generally understood by the worker in the technical field of the invention.

"A", "an" and "the" refer in the document to both the singular and the plural form unless clearly understood differently in the context. "A ventilation opening" means for example one or more than one ventilation opening.

The terms "include", "including" and "provide with" are synonyms and are inclusive of open terms that indicate the presence of what follows, and that do not exclude or prevent the presence of other components, characteristics, elements, members, steps, known from or described in the state of the art.

The citation of numeric intervals by means of end points includes all integers, fractions and/or real numbers between the end points, including these end points.

In a first aspect, the invention relates to a pen for the treatment of dermatological disorders, such as warts, by means of a coolant, which pen comprises: a distal part comprising a holder for the storage of a coolant and a proximal part comprising an applicator for the administration of the coolant to the dermatological surface to treat, which parts extend axially and which parts are in coolant communication by means of a coolant passage in the proximal part, in which a valve body is provided for closing off and/or opening the passage, in which the passage is provided with at least one bypass for the coolant.

The term "holder" or "gas cartridge" are used in an exchangeable way, but refer to the same part, they are synonyms.

The pen according to the present invention is appropriate for the treatment of dermatological disorders, such as warts, by means of low temperatures that can be reached at the applicator of the pen. These low temperatures are generated when a liquid coolant, with a low boiling point, evaporates quickly at the applicator at environmental temperature or at body temperature of a human body. The heat required for the evaporation of the liquid coolant is withdrawn from the applicator, so that this applicator cools down to low temperatures. In other words, the applicator is cooled down to low temperatures by means of evaporative cooling. The use of an applicator cooled down to a low temperature at the dermatological area to treat causes the destruction of present dermatological disorders by killing the cells. The obtained evaporative cooling achieves temperatures that are sufficiently low for the treatment of dermatological disorders, without causing hypothermia and/or without undesired interaction of the low temperatures with areas that do not require treatment, such as, for example, healthy skin tissue surrounding a dermatological disorder. Several dermatological disorders such as for example warts, hyperpigmentation and fibroma, can be treated by using the obtained evaporative cooling.

The distal part of the pen extends axially and comprises a holder for the storage of coolant. The holder preferably contains a coolant under increased pressure, comprising one or more chemical agents, which can deliver temperatures that are sufficiently low for treatment of several dermatological disorders such as for example warts, hyperpigmentation and fibroma. Dimethyl ether, n-butane, isobutene, propane, nitrogen, dinitrogen oxide and/or halogenated hydrocarbons such as, for example, tetrafluoromethane, trifluoromethane and 1,1,2-tetrafluoroethane are appropriate examples of chemical agents. A skilled worker will understand that because of the relatively high internal pressure that is present in the holder, chemical agents can be present in the form of a liquid or a gas/liquid mixture. For coolants in the form of a liquid, the term liquid coolant is used. For coolants in the form of a gas, the term gaseous coolant is used. Moreover, a skilled worker will understand that a coolant can consist of several different chemical agents in order to decrease the internal pressure of the holder necessary for achieving a desired boiling point. Several materials, such as for example steel and aluminium, are appropriate as a material for the holder. The holder preferably forms a closed volume, except for an opening at an end of the holder that is positioned closest to the proximal part of the pen. At storage, this opening of the holder is preferably provided with a closure for keeping the coolant in the holder during storage. Several materials, such as for example steel, rubber, plastic and/or a synthetic material are appropriate as a material for the closure. A skilled worker will understand that the type of material for the holder and the closure can be chosen depending on the resistance to corrosion as a result of contact with the coolant, and the possibility to resist the high internal pressure levels and the low temperatures when enclosing a coolant, such as, for example, liquid dinitrogen oxide under increased pressure.

The proximal part comprises an applicator for administration of the coolant at the dermatological area to treat. The applicator is preferably located at the proximal side of the proximal part. Moreover, at least a part of the applicator, at its proximal side, is preferably exposed to the environment. At administration, liquid coolant will evaporate at the applicator so that the applicator is cooled down to low temperatures and the cooled-down applicator will be brought into contact with the dermatological area to treat. The proximal part of the pen extends axially. The axially extending proximal and distal part of the pen are in coolant communication with each other by means of a coolant passage that is located in the proximal part. The coolant passage is defined as a preferably axially extending opening in the proximal part in which flow of the coolant is possible. Coolant communication means that, at the connection of the proximal part and the distal part, these parts are connected to each other so that coolant from the holder can flow to the coolant passage. In the coolant passage, a valve body is provided for closing off and/or opening the coolant passage. When closing coolant passage by means of the valve body, the valve body constitutes a barrier for the coolant so that the coolant cannot flow to the applicator. When opening the coolant passage, the barrier for the coolant by means of the valve body is raised and the coolant can flow in the proximal part through the coolant passage to the applicator. The valve body can be any construction that can create a barrier in the coolant passage that can be raised, if required. The valve body occupies a particular volume of the coolant passage. The coolant passage is provided with at least one bypass for the coolant. A bypass is defined as a local abnormality in shape of the coolant passage offering an alternative for the flow of coolant for a part of the coolant passage, via the bypass, to another part of the coolant passage. Via the bypass, the velocity of the coolant can be regulated. The pen according to the present invention preferably relates to a compact pen, especially for home use, that is compact, easy and safe to use, can deliver efficient evaporative cooling, has a low cost price and is disposable.

According to a preferred embodiment, said pen is a wart pen for the treatment of warts, comprising:
  a cartridge housing 1 in which a gas cartridge 2 is placed at least temporarily, which gas cartridge 2 contains a coolant under increased pressure;
  a dose-measuring device with a coolant and provided with one or more housings 3, 4, 6, 10, which dose-measuring device is appropriate for being attached at a distal side to a cartridge housing 1, which dose-measuring device is equipped at a proximal side with an applicator 7 for administrating low temperatures to one or more warts to treat, which dose-measuring device comprises distally to the applicator 7 a perforator 5 which is arranged for puncturing the gas cartridge 2 and which dose-measuring device is provided between the applicator 7 and the perforator 5 with a valve body for closing off and/or opening the coolant passage;
  a closing cap 11 appropriate for being positioned in a removable manner at or being attached to the proximal side of the dose-measuring device;
  in which the cartridge housing 1 and/or at least one housing 3, 4, 6, 10 of the dose-measuring device is fabricated of a synthetic material reinforced with glass fibres.

The wart pen according to the present invention is appropriate for the treatment of warts by the low temperatures, preferably lower than −65° C., more preferably lower than −70° C. and most preferably lower than −95° C., that can be reached at the applicator 7 of the wart pen. These low temperatures are generated when a liquid coolant, with a low boiling point, preferably lower than 10° C., more preferably lower than 0° C., still more preferably lower than −50° C. and most preferably lower than −85° C., evaporates quickly at the applicator 7 at environment temperature or at the body temperature of a human body. The heat required for the evaporation of the liquid coolant is withdrawn from the applicator, so that this applicator 7 cools down to low temperatures. In other words, the applicator 7 is cooled down to low temperatures by means of evaporative cooling. The use of an applicator 7 cooled down to a low temperature at one or more warts causes the destruction of the one or more warts by killing the cells. The obtained evaporative cooling reaches temperatures that are sufficiently low for the treatment of warts, preferably a temperature lower than −60° C., more preferably a temperature lower than −70° C. and most preferably a temperature lower than −75° C., without causing hypothermia and/or without undesired interaction of the low temperatures with areas that do not require treatment, such as, for example, healthy skin tissue surrounding the wart. Several other dermatological disorders than warts such as for example hyperpigmentation and fibroma, can also be treated by using the obtained evaporative cooling.

Gas cartridges 2 are provided for containing a coolant under increased pressure. Therefore, a gas cartridge 2 constitutes in closed position a closed volume in which the coolant can be stored. The gas cartridge 2 preferably contains an opening that, in unused condition of the gas cartridge 2, is closed off by a closure, which closure serves to keep the coolant within the gas cartridge 2 in unused condition. A coolant comprises one or more chemical agents. A coolant appropriate for use in the present invention can deliver temperatures that are sufficiently low for the treatment of warts. Dimethyl ether, n-butane, isobutene, propane, nitrogen, $N_2O$ and/or halogenated hydrocarbons such as, for example, tetrafluormethane, trifluormethane and 1,1,1,2-tetrafluorethane are examples of chemical agents that are appropriate for use as components of a coolant that is suitable for the present invention. A skilled worker will understand that a coolant can consist of several different chemical agents in order to decrease the internal pressure of the gas cartridge 2 necessary for achieving a desired boiling point. A skilled worker will also understand that because of the high internal pressure that is present in the holder, a coolant can be present in the form of a liquid or a gas/liquid mixture. For coolants in the form of a liquid, the term liquid coolant is used in this text. For coolants in the form of a gas, the term gaseous coolant is used in this text. Several materials, such as for example steel and aluminium, are appropriate as a material for the holder.

Several materials, such as for example steel, rubber, plastic and/or a synthetic material are appropriate as a material for the closure of the gas cartridge 2. A skilled worker will understand that the type of material for the gas cartridge 2 and the closure of the gas cartridge can be chosen depending on the resistance to corrosion as a result of contact with the coolant, and the possibility to resist the high internal pressure levels and the low temperatures when enclosing a coolant, such as, for example, liquid dinitrogen oxide under increased pressure. In the wart pen according to the present invention, the gas cartridge 2 is at least partially located in a specially designed cartridge housing 1.

The dose-measuring device of the wart pens according to the present invention are arranged to receive coolant from the gas cartridge 2 and to dose this coolant to the applicator 7 of the dose-measuring device. The dose-measuring device contains a coolant passage and is provided with one or more housings 3, 4, 6, 10. The coolant passage constitutes a passage through the dose-measuring device, in which coolant from the gas cartridge 2 can flow through the dose-measuring device to the applicator 7, when the coolant from the gas cartridge 2 is put at disposal for the dose-measuring device. The one or more housings 3, 4, 6, 10 of the dose-measuring device is arranged to contain other components of the dose-measuring device and to contain a coolant. The dose-measuring device has a distal side and a proximal side. The dose-measuring device can be attached to the cartridge housing 2 by means of the distal side.

The proximal side of the dose-measuring device is equipped with an applicator 7 for administering low temperatures to one or more warts to treat. The applicator 7 preferably has a porous structure and is preferably constituted of a material with a high thermal conductivity and is configured to spread liquid coolant while the liquid coolant withdraws heat from the applicator 7 for evaporation of liquid coolant. Sintered metals, such as for example sintered copper, aluminium or steel can also be used as material for the applicator 7. Moreover, the applicator 7 can also partially or in whole be fabricated of a porous synthetic material such as, for example, porous polyethylene. The applicator 7 comprises an administration surface, by which low temperatures can be administered to one or more warts to treat. The administration surface of the applicator 7 preferably corresponds to the side of the applicator 7 that is most distally located with respect to the wart pen. The part of the applicator not located at the administration surface is preferably protected from the environment. Distally to the applicator 7, the dose-measuring device comprises a perforator 5 that is arranged to puncture the gas cartridge 2. Puncturing the closure of the gas cartridge 2 by means of the perforator 5 is preferably used for putting at disposal the coolant, from the gas cartridge 2 for the dose-measuring device.

The perforator 5 preferably consist of a material that is resistant to corrosion by contact with the coolant and that can resist to increased pressure levels exercised by the coolant as well as the low temperatures of the coolant. In addition, the perforator 5 preferably consists of a material that can puncture the closure. For example, the perforator 5 is made of metal. The perforator preferably is hollow so that the coolant can flow through the perforator.

Between the applicator 7 and the perforator 5, the dose-measuring device is provided with a valve body for closing off and/or opening the coolant passage. When a coolant is put at the disposal of the dose-measuring device, a closed valve body will ensure the coolant can only flow to the valve body, while an opened valve body allows a flow of the coolant through the valve body to the applicator 7.

The closing cap 11 of the wart pen according to the present invention is appropriate for being positioned in a removable manner at or being attached to the proximal side of the dose-measuring device. The positioning and attachment of the closing cap 11 at the proximal side of the dose-measuring device causes the full enclosure and hence protection of the applicator 7. The closing cap 11 is preferably arranged to enclose the applicator 7 in a fluid-tight manner. The term "fluid-tight" in this text means that there is a minimum leakage of liquid coolant, in the case this coolant is present in the applicator 7. The term "minimum leakage" in this text means that maximum 5% of the liquid coolant is released to the environment, when the closing cap 11 is attached to the proximal side of the dose-measuring device. In a further preferred embodiment, maximum 0.3%, more preferably maximum 1.0% and most preferably maximum 0.1% of the liquid coolant is released to the environment, when the closing cap 11 is attached to the proximal side of the dose-measuring device. The minimizing of the release or loss of liquid coolant to the environment, at the applicator 7, ensures that the liquid coolant can be optimally used for cooling down the applicator 7 by means of evaporative cooling. When coolant is present at the applicator 7, the closing cap 11 moreover provides an isolation of the applicator 7 with respect to the environment, so that the evaporative cooling of the applicator 7 can be realized efficiently. For using low temperatures via the applicator 7 at one or more warts to treat, it is desirable to not to position and/or to attach the closing cap 11 at the proximal side of the dose-measuring device. The closing cap 11 is preferably made of polymers and preferably produced via injection moulding in a mould. The closing cap 11 is preferably made of styrene acryl nitrile.

At least one housing 3, 4, 6, 10 of dose-measuring device and/or cartridge housing 1 of the wart pen according to the present invention is made of synthetic material reinforced with glass fibres. A synthetic material reinforced with glass fibres is a strong material with a light weight that is cheaper than the high-quality lightweight materials such as aluminium and carbon fibre. This makes a synthetic material reinforced with glass fibres extremely suitable as a material for the cartridge housing 1 and/or at least one housing 3, 4, 6, 10 of the dose-measuring device, since these housings can, for safety measures and for guaranteeing an efficient use of the wart pen, resist the high pressure levels cause ty the coolant under increased pressure. An appropriate example of a synthetic material reinforced with glass fibres is polyoxymethylene reinforced with glass fibres.

According to an embodiment of the first aspect of the invention, the cartridge housing 1 and/or at least one housing 3, 4, 6, 10 of the dose-measuring device have a maximum compressive force of 1850 N to 6400 N, measured according to ASTM D695-10. Similar values of maximum compressive force for housings of the wart pens are important for resisting the high pressure levels exercised by a coolant under increased pressure that is present in the wart pen.

According to a preferred embodiment of the pen, the bypass does not extend axially.

Since the coolant passage preferably extends axially, considering the proximal part of the pen extends axially, the non-axial orientation of the bypass can be used for regulating the velocity of the coolant, when coolant passes the bypass. The angle between the bypass and the axially oriented coolant passage, according to the direction of the distal part to the proximal part of the pen, is preferably located between 0.5° and 90°, and more preferably between 20° and 80°.

According to a more preferred embodiment of the pen, the bypass extends radially. The radial extension of the bypass ensures that, when an end of the bypass is located in the radial direction outside the coolant bypass, the other end of the bypass will end in the coolant bypass.

According to another preferred embodiment of the pen, the diameter of the bypass is smaller than the diameter of the coolant passage.

When the coolant is moved from the bypass to the coolant passage, the coolant will, as a result of the increase in the available volume, be subjected to a pressure decrease together with a velocity increase. This velocity increasing effect results in a regulation and more in particular in an acceleration of the flow of the coolant and this acceleration ensures the freezing phenomena at the bypass, and the environment of the coolant passage where the coolant leaves the bypass, are limited. In addition, this velocity increasing effect provides a quicker delivery of coolant to the application, which coolant can be used at the applicator for evaporative cooling.

According to another preferred embodiment of the pen, the bypass is located between the applicator and the valve body, and the bypass is positioned against the valve body.

The location of the bypass between the applicator and the valve body, positioned against the valve body, has as a function that the bypass, when administering the valve body, in which a flow of coolant along the valve body is possible, offers an alternative path for the flow of the coolant. The construction of the valve body, the coolant passage and the bypass are preferably such that the coolant prefers the bypass for the flow along the valve body. The advantages of the use of a bypass are described above.

According to another preferred embodiment of the pen, the valve body contains a ball that is resiliently bearing. The ball is configured to close off the part of the coolant passage proximally to the valve body. The resilient bearing of the ball means that the ball rests on a spring in the direction of the distal part of the pen. The axis of the spring is preferably oriented according to the length axis of the pen. The spring supports the position of the ball. At presence of coolant at the valve body, an internal pressure resulting from the coolant contributes to the connection of the ball against the proximal part of the coolant passage. When an external pressure is exercised on the proximal part of the pen, oriented against the force of the spring and the internal pressure, the spring will contribute to maintaining the position of the ball with respect to the axis of the spring. The ball and spring preferably consist of a material that is resistant to corrosion by contact with the coolant and that can resist to high internal pressure levels exercised by the coolant as well as the low temperatures of the coolant. The ball and spring can for example be made of metal, preferably stainless steel.

According to another preferred embodiment of the pen, the applicator contains an administration surface and the average pore size of the applicator decreases in the axial direction to the administration surface.

The administration surface corresponds to the surface located at the side of the applicator that is situated proximally with respect to the pen. At the administration surface, the applicator is exposed to the environment. This administration surface is the part of the applicator where the low temperatures, obtained via evaporative cooling, can be administered to a dermatological disorder, such as for example a wart, hyperpigmentation or fibroma. The applicator preferably has a porous structure and is preferably constituted of a material with a high thermal conductivity and is configured to spread liquid coolant while the liquid coolant withdraws heat from the applicator for evaporation of liquid coolant. Sintered metals, such as for example sintered copper, aluminium or steel can also be used as material for the applicator. Moreover, the applicator can also partially or in whole be fabricated of a porous synthetic material such as, for example, porous polyethylene. The part of the applicator not located at the administration surface is preferably protected from the environment. Loss of cold via the non-functional part of the applicator, that is the part of the applicator that is not brought into contact with the surface to treat, is avoided in this way. The applicator can have a porosity of 10% to 95%. The applicator preferably has a porosity of 20% to 70%, and more preferably of 35% to 65%. The applicator can have an average pore size of 1 µm to 350 µm. The applicator preferably has an average pore size of 1 µm to 750 µm, more preferably of 10 µm to 650 µm, even more preferably 20 to 500 µm and most preferably 150 to 250 µm.

Decrease of the average pore size of the applicator, in the axial direction of the applicator to the administration surface, results in a higher storage of cold. In other words, the decrease of the average pore size provides a concentration of cold in the direction of the administration surface, allowing a more efficient use of the evaporative cooling. The decrease of the average pore size, in the axial direction of the applicator to the administration surface, should be seen as a decrease of the average pore size per transversal or perpendicular surface with respect to the axial direction.

According to another preferred embodiment of the pen, the average pore size of the applicator, in the axial direction to the administration surface, decreases from 60-350 µm to 1-55 µm. The average pore size of the applicator, in the axial direction to the administration surface, preferably decreases from 60-250 µm to 1-50 µm, and more preferably from 65-150 µm to 10-50 µm. Along the axial direction of the applicator, the porosity of the applicator, in which the porosity is considered per transversal or perpendicular surface with respect to the axial direction, can have a variation of at most 30%. This variation of the porosity preferably amounts to at most 20% and more preferably at most 15%. Combined with this variation of the porosity of at most 30%, preferably at most 20% and most preferably at most 15%, the average pore size of the applicator, in the axial direction of the administration surface, preferably decreases from 60-350 µm to 1-55 µm. Combined with this variation of porosity of at most 30%, preferably at most 20% and most preferably at most 15%, the average pore size of the applicator, in the axial direction of the administration surface, more preferably decreases from 60-250 μm to 1-50 μm. Combined with this variation of the porosity of at most 30%, preferably at most 20% and most preferably at most 15%, the average pore size of the applicator, in the axial direction of the administration surface, still more preferably decreases from 65-150 μm to 10-50 μm.

According to another preferred embodiment, said applicator contains a transformable foam, more preferably a transformable foam with an open cell structure. The material of said foam is preferably polyurethane (PU) and more preferably a polyester polyurethane. The hardness of said foam is preferably 4 to 30 kPa, more preferably 5 to 25 kPa, still more preferably 6 to 20 kPa, even more preferably 7 to 15 kPa and most preferably 8 to 10 kPa. The advantage is that the applicator deforms when it is pushed against the wart. As a result, the contact surface between the applicator and the wart increases and an efficient heat transfer can occur and the larger part of the wart is exposed to the generated cold in the applicator. Further, a pressure is applied during the application of the applicator to the wart so that the pores of the foam adjacent the applicator tip or the administration surface, first and foremost melt, and then be at least partially compressed. This hampers the flow of the coolant in this zone, resulting in a greater Joule-Thomson effect, causing the cooling effect in this zone to be larger. The pores further away from the applicator or the administration surface stay frozen for longer and maintain their dimensions during use. Preferably, the dimensions of the pores adjacent the applicator tip or the administration surface will be compressed during the application of the applicator on the wart by 20 to 80%, more preferably by 30 to 70%, still more preferably by 40 to 60% and most preferably by 50%.

In a preferred embodiment, said foam is comprising pores having a pore size of 100 μm to 1000 μm, more preferably from 200 to 900 μm, still more preferably 300 to 800 μm, even more preferably from 400 to 700 μm and most preferably from 450 to 650 microns. Such a pore size ensures that the flow of the coolant is hampered enough in order to obtain the desired cooling effect, but also does not lower the speed of the flow too much.

In a preferred embodiment, said applicator has a density of 19 to 67 kg/m$^3$, preferably of 24 to 62 kg/m$^3$, more preferably of 29 to 57 kg/m$^3$, still more preferably of 34 to 52 kg/m$^3$ and most preferably of 39 to 47 kg/m$^3$. This ensures that coolant flows quickly through the applicator, thus allowing to obtain a low temperature.

In a preferred embodiment, said applicator has a maximum diameter of 3 to 10 mm, preferably 4 to 9 mm, more preferably 5 to 8 mm and most preferably 6 to 7 mm. Such a diameter provides a sufficiently large contact surface between the applicator and the wart.

According to an embodiment of the first aspect of the invention, the applicator 7 has a volume of 0.05 cm$^3$ to 1.00 cm$^3$. The applicator 7 preferably has a volume of 0.150 cm$^3$ to 0.500 cm$^3$. The applicator 7 can occur in several geometries. The applicator 7 can thus amongst other things have the shape of a bar, cube or cylinder. The applicator 7 preferably has the shape of a cylinder. Said volumes and geometries are appropriate for obtaining an applicator 7 with an administration surface that desirably is dimensioned for treating one or more warts. Moreover, said volumes are sufficiently large for allowing a sufficient degree of evaporative cooling to occur in the applicator 7 by means of a coolant.

In a preferred embodiment, the pen is designed so that the coolant flows through the applicator in a direction from the applicator tip to the applicator tip or administration surface, in other words, in an axial direction toward the administration surface. Among other, this makes the cooling effect, as a result of the Joule-Thomson effect, the greatest at the applicator tip or the administration surface.

The term "applicator tip" refers to the tip of the applicator that is located farthest from the gas cartridge. The term "administration surface" refers to the portion of the applicator that, during the use of the pen, can make contact with the wart. "Applicator" and "administration surface" may mean the same thing, depending on the geometry and transformability of the applicator.

In a preferred embodiment, the inner volume of the closing cap surrounding the applicator comprises a decreasing diameter, wherein the diameter decreases in the direction of the applicator holder to the applicator tip or administration surface, more preferably, said inner volume comprises a conical part. As a result, the flow of coolant is hampered in the zone round the applicator tip or administration surface, which enhances the Joule-Thomson effect and which makes this zone the coldest. Also, this shape of the closing cap will bring the not yet vaporized coolant to the applicator tip or administration surface, so that it can evaporate there and eventually reduce the temperature.

In a preferred embodiment, the shortest distance between the applicator tip or the administration surface and the inner volume of the closing cap is 0.0 to 5.0 mm, preferably 0.1 to 4.0 mm, more preferably 0.2 to 3.0 mm, still more preferably 0.3 to 2.0 mm, even more preferably 0.4 to 1.5 mm and most preferably 0.5 to 1.2 mm, such as 0.7 or 1.0 mm. Such a shortest distance between the applicator tip or the administration surface and the inner volume of the closing cap ensures that the flow of coolant around the applicator tip or the administration surface is hampered, allowing for a greatest cooling effect to occur in this zone. In a further preferred embodiment, the shortest distance between the inner volume of the closing cap and the applicator at the place where the applicator leaves the applicator holder, is from 2.0 to 5.0 times larger, more preferably 2.5 to 4.5 times larger, even more preferably 3.0 to 4.0 times larger than the shortest distance between the applicator tip or administration surface and inner volume of the closing cap. This also ensures that the flow of coolant is most hampered around the applicator tip or administration surface.

According to an embodiment of the first aspect of the invention, the dose-measuring device contains a device for flow control of the coolant. This refers to flow control of the coolant that can flow in an opened position of the valve body through the valve body to the applicator 7. By means of flow control, the flow of the coolant can be regulated so that the coolant can flow in a sufficient amount and with a sufficient velocity to the applicator 7, so that a desired degree of evaporative cooling in the applicator 7 can occur. Without flow control, the velocity of the coolant would be too high to use the wart pens in an efficient way for the intended purpose. In the state of the art, a porous filter is usually used for flow control of the coolant in wart pens. Such a porous filter could also be used for flow control in the wart pens according to the present invention. However, the present invention provides a device for flow control, rendering an additional component for flow control, such as, for example, a porous filter, superfluous, which is a way to reduce the cost price of a wart pen. As said above, a coolant passage runs through the dose-measuring device, as a result of which coolant from the gas cartridge 2 can flow through the dose-measuring device to the applicator 7. According to a preferred embodiment, the coolant passage is locally strongly narrowed down in the part adjoining a proximal part located with respect to the valve body. This narrowing will ensure a flow control of the coolant. After this local narrowing, the coolant passage will again be broadened in the direction of the applicator 7. Said narrowing is preferably provided in the bypass.

According to another preferred embodiment of the pen, the applicator is provided with colour indications that are used to indicate specific values or intervals of medium pore size, porosity or a combination of medium pore size and porosity, of the applicator. Intervals are preferably indicated by the colour indications. The applicator can be divided into one or more segments that correspond to different intervals of medium pore size, porosity or a combination of medium pore size and porosity. As colour indications, said segments are preferably all provided with a different colour. For this, any colours can be selected. For colouring said segments, colouring agents can be used. Colouring agents can be dyes, pigments, inks, paints, etc. A dye is a coloured substance that typically has affinity for the substrate or material to which it is applied. The dye is typically applied in a solution (for example water based, organic solvent based or oil based) and usually requires an etching agent to be fixed to a substrate or material. Colouring agents such as dyes and pigments show their specific colour because they absorb particular wave lengths of the light stronger than other materials. Contrary to a dye, a pigment is generally insoluble, and is generally used as a powder or as a liquid dispersion (for example water based, organic solvent based or oil based). Non-limiting examples of dyes are acridin, anthraquinon, cumarin-, difenylmethane, quinolon-, stilbene and trifenylmethane compounds. Non-limiting examples of pigments are naphtol, benzimidazolon, indanthron and flavanthron. The advantage of colouring the applicator is that errors with respect to the orientation of the applicator during the assembly of the pen can be avoided. For a pen according to the present invention, the applicator of the pen is for example provided with two different colours, in which one colour is used for indicating an interval of particular average pore sizes while the other colour is used for indicating an interval with smaller average pore sizes. A desired orientation based on the average pore size can easily be verified by means of the used colours.

According to another preferred embodiment of the pen, the proximal part of the pen further comprises a perforator, which perforator is located between the valve body and the distal end.

As said above, at storage, the coolant is preferably enclosed by the holder that constitutes a closed volume, except for an opening at the end of the holder that is located closest to the proximal part of the pen, which opening is closed off by a closure. The perforator is configured to puncture the closure, present at storage of the coolant in the holder. As a result, the coolant can flow out of the holder via the opening in the direction of the proximal part of the pen. The perforator preferably consist of a material that is resistant to corrosion by contact with the coolant and that can resist to high internal pressure levels exercised by the coolant as well as the low temperatures of the coolant. In addition, the perforator preferably consists of a material that can puncture the closure. For example, the perforator is made of metal. The perforator preferably is hollow so that the coolant can flow through the perforator.

According to another preferred embodiment of the pen, the pen further comprises a removable closing cap for protecting the applicator.

The removable closing cap can be placed onto the proximal part of the pen and the closing cap thus protects the part of the applicator that would otherwise be exposed to the environment. The term "removable" in this text means that when the closing cap is placed onto the pen, this closing cap can subsequently again be removed. The closing cap is preferably arranged for closing of the applicator in a liquid-tight manner. The term "fluid-tight" in this text means that there is a minimum leakage of liquid coolant, in the case this coolant is present in the applicator. The term "minimum leakage" in this text means that maximum 7% of the liquid coolant is released to the environment, when the closing cap is mounted to the pen. In a further preferred embodiment, maximum 4%, more preferably maximum 1% and most preferably maximum 0.1% of the liquid coolant is released to the environment, when the closing cap is mounted to the pen. The minimizing of the release or loss of liquid coolant to the environment, at the applicator, ensures that the liquid coolant can be optimally used for cooling down the applicator by means of evaporative cooling. In a preferred embodiment, the closing cap is made of polymers and preferably produced via injection moulding in a mould. The closing cap is preferably made of styrene acrylonitrile.

According to another preferred embodiment of the pen, the closing cap is composed for a first housing, provided with an open proximal and a closed distal end, and a second housing, provided with a closed proximal end and an open distal end, that is accommodated at least partially by the first housing and that, when the closing cap is placed onto the pen, contains the applicator at least partially, but preferably in whole and of which the distal part is provided with a connecting mechanism to connect to the proximal part of the pen or dose-measuring device.

When the closing cap is mounted on the proximal part of the pen, the second housing of the closing cap protects the part of the applicator that would otherwise be exposed to the environment and the second housing also provides a liquid-tight closure of the applicator. The connecting mechanism of the open distal part of the second housing of the closing cap can have different shapes, as long as this connecting mechanism allows removing the closing cap, after mounting this closing cap onto the pen. Between the closed proximal part of the second housing of the closing cap and the first housing of the closing cap, the environmental air can move. The present air layer provides an isolation of the first housing with respect to the second housing. This is important when the applicator is cooled down by means of evaporative cooling and the closing cap is mounted onto the pen for protecting and closing off the applicator in an liquid-tight manner. The second housing of the closing cap can in this way be cooled down significantly. The isolation of the first housing of the closing cap by means of the air layer ensures the closing cap can be grasped safely by a user of the pen, without experiencing any adverse effects of the low temperatures, at the second housing.

According to another preferred embodiment of the pen, the connecting mechanism of the closing cap comprises at least one projecting part that fits in at least one recess in the proximal part of the pen.

Both the projection and the recess can have arbitrary shapes, as long as the projects fits into the recess. The connecting mechanism of the closing cap preferably contains two projections, and more preferably three projections, that can all simultaneously be placed into a corresponding number of recesses of the proximal part of the pen. The necessity of having the projections fit into the recesses is a safety mechanism that avoids unintentional connection of the closing cap to the proximal part of the pen.

According to another preferred embodiment of the pen, the proximal part of the pen, the closing cap or both are the proximal part of the pen and the closing cap is provided with a ventilation opening for removing a gaseous coolant.

A ventilation opening is a gap at the proximal part of the pen, the closing cap or both the proximal part of the pen and the closing cap, where gaseous coolant, generated at the evaporative cooling, can escape from the pen. When the closing cap is placed onto the proximal part of the pen for protecting and closing off the applicator in a liquid-tight manner, the gaseous coolant generated at the evaporative cooling be withdrawn from the applicator via ventilation openings. In this way, an overpressure in the device can be avoided. Moreover, the ventilation openings constitute a safety mechanism for avoiding an overpressure if the gaseous coolant is formed unintentionally in the pen. The unintentional formation of gaseous coolant can occur exceptionally if the environment pressure is so high that the pressure to which the coolant is subjected, become so high that the coolant can flow through the coolant passage to the applicator, this exceptionally without exercising an external pressure, directed against the internal pressure caused by the coolant, onto the proximal part of the pen.

In a preferred embodiment, the pen is a wart pen for the treatment of warts, comprising:
  a cartridge housing (1) in which a gas cartridge (2) is placed at least temporarily, which gas cartridge (2) contains a coolant under increased pressure;
  a dose-measuring device with a coolant and provided with one or more housings (3, 4, 6, 10), which dose-measuring device is appropriate for being attached at a distal side to a cartridge housing (1), which dose-measuring device is equipped at a proximal side with an applicator (7) for administrating low temperatures to one or more warts to treat, which dose-measuring device comprises distally to the applicator (7) a perforator (5) which is arranged for puncturing the gas cartridge (2) and which dose-measuring device is provided between the applicator (7) and the perforator (5) with a valve body for closing off and/or opening the coolant passage;
  a closing cap (11) appropriate for being positioned in a removable manner at or being attached to the proximal side of the dose-measuring device;
  in which the cartridge housing (1) and/or at least one housing (3, 4, 6, 10) of the dose-measuring device is fabricated of a synthetic material reinforced with glass fibres.
  in which then pen contains one, several or all of the following options:
    the cartridge housing (1) and/or at least one housing (3, 4, 6, 10) of the dose-measuring device have a maximum compressive force of 1850 N to 6400 N, measured according to ASTM D695-10.
    the applicator (7) has a volume of 0.05 cm$^3$ to 1.00 cm$^3$;
    the dose-measuring device contains a device for flow control of the coolant; and/or,
    the closing cap (11) is composed for a first housing of the closing cap, provided with an open proximal end and a closed distal end, and a second housing of the closing cap, provided with a closed proximal end and an open distal end, that is accommodated at least partially by the first housing of the closing cap and that, when the closing cap (11) is placed at the proximal side of the dose-measuring device, contains the applicator (7) in whole and of which the open distal end is provided with a connecting mechanism to connect to the proximal side of the dose-measuring device.

A second aspect of the invention relates to a method for the administration of a pen according to the present invention, which method comprises:
  providing the pen for the treatment of dermatological disorders, which pen is provided with a removable closing cap;
  flowing a coolant under increased pressure from the holder for the storing of the coolant to the valve body;
  exercising an external pressure on the proximal part of the pen for the administration of the valve body, which external pressure is exercised in opposite direction to the pressure exercised by the coolant;
  flowing the coolant past the valve body to the applicator;
  realizing the evaporative cooling at the applicator;
  removing the closing cap from the pen.

In the case of a pen for the treatment of dermatological disorders according to the present invention, the coolant will be able to flow to the valve body, when the coolant under higher pressure can flow out of the holder. For the coolant to flow out of the holder, it is necessary that the coolant can leave the holder through an opening. The pen is preferably positioned in an upward position with the proximal part of the pen directed downwardly, so that gaseous coolant is located further from the proximal part of the pen than liquid coolant. The advantage is that especially liquid coolant can be located at the valve body, which coolant can be used at the administration for evaporative cooling of the applicator. Administration of the valve body means that an external pressure is exercised onto the proximal part of the pen, which external pressure is exercised in the opposite direction to a pressure that is exercised by the coolant. For the administration of the valve body by exercising an external pressure, it is required that the proximal part of the pen is provided with a removable closing cap. For the administration of the valve body, the external pressure is thus exercised onto this removable closing cap and the exercised pressure is transferred to the proximal part of the pen.

When mounted onto the proximal part of the pen, the closing cap protects the part of the applicator that would otherwise be exposed to the environment. The closing cap is preferably arranged for closing of the applicator in a liquid-tight manner. The removable closing cap is provide with a connecting mechanism to connect to the proximal part of the pen. The connecting mechanism can have different shapes, as long as this connecting mechanism allows removing the closing cap, after mounting this closing cap onto the pen. The connecting mechanism of the closing cap preferably comprises at least one projecting part that fits in at least one recess in the proximal part of the pen. Both the projection and the recess can have arbitrary shapes, as long as the projection fits into the recess. The connecting mechanism of the closing cap preferably contains two projections, and more preferably three projections, that can all simultaneously be placed into a corresponding number of recesses of the proximal part of the pen. The necessity of having the projections fit into the recesses is a safety mechanism that avoids unintentional connection of the closing cap to the proximal part of the pen, and thus unintentional administration of the valve body.

The exercise of the external pressure in the opposite direction of a pressure that is exercised by the coolant provides an increase of the pressure at the valve body, as a result of which the coolant seeks a way out. The coolant preferably finds this way out in the form of a bypass that is positioned between the applicator and the valve body, and is located against the valve body. As a result of the exercised external pressure, the coolant can flow past the valve body to the applicator. The exercise of an external pressure on the proximal part of the pen, in opposite direction to a pressure exercised by the coolant, offers the advantage that only a flow of coolant past the valve body is allowed as long as this external pressure is maintained. At the preferably porous structure of the applicator, evaporation of liquid coolant provides a gaseous coolant for withdrawing the heat from the applicator and thus for providing an evaporative cooling of the evaporator. When exercising the external pressure, the closing cap is preferably mounted onto the proximal part of the pen, so that the applicator is protected. Moreover, mounting the closing cap is important because the closing cap closes off the applicator in a liquid-tight manner, so that as much liquid coolant as possible can be used for the evaporative cooling at the applicator. While the external pressure is sued, it is recommended to maintain the external pressure for a while, in other words, to wait a moment, until the applicator has reached a sufficiently low temperature for starting an efficient cold treatment of skin disorders. Sufficiently low temperatures are temperatures lower than −65° C., preferably between −70° C. and −95° C. In order to reach these temperatures, the external pressure should be maintained for 1 s to 5 s. This are the durations in case the closing cap is mounted to the proximal part of the pen while the external pressure is applied. Before the administration surface of the cooled down applicator can be placed onto the dermatological surface to treat, the closing cap should be removed from the pen.

According to a preferred embodiment of the method, the method comprises the following steps:
puncturing the holder for the storage of the coolant with a perforator.

Adding this step to the method allows the consumer to create an opening in the holder for the storage of the coolant just before using the pen so that this coolant can flow to the valve body via the coolant passage. The advantage is that the holder can be closed off until use of the pen, which prevents possible loss of coolant before using the pen.

FIG. 1 is an exploded view of a possible embodiment of the pen according to the present invention. This figure clearly shows the different parts of the possible embodiment of the pen and their position with respect to each other. As shown in FIG. 1, the embodiment of the pen comprises a back housing (1), a gas cartridge (2), a valve housing (3), a perforator holder (4), a perforator (5), an applicator holder (6), an applicator (7), a ball (8), a spring (9), a front housing (10), a closing cap (11), a first O-ring (12), a second O-ring (13) and a third O-ring (14). The first O-ring (12), the back housing (1) and the gas cartridge (2) can be considered as parts of the distal end of the pen. The valve housing (3), the perforator holder (4), the perforator (5), the applicator holder (6), the applicator (7), the ball (8), the spring (9), the front housing (10), the second O-ring (13) and the third O-ring (14) can be considered as parts of the proximal part of the pen. The closing (11) can be mounted removably onto the proximal part of the pen. The first (12), second (13) and third O-ring (14) are respectively positioned between gas cartridge (2) and perforator holder (4), between ball (8) and applicator holder (6) and between applicator holder (6) and valve housing (3) to avoid losses of coolant. A non-limiting example of a material that is appropriate for the O-rings is polyetheretherketon. The back housing (1) is configured to contain the gas cartridge (2) comprising coolant. The perforator holder (4) partially contains the perforator (5). The part of the perforator (5) that is not contained in the perforator holder (4), is configured for puncturing the gas cartridge (2). The valve housing (3) can be mounted onto the back housing (1) and is configured for containing the perforator holder (4), ball (8) and spring (9), as well as a part of the applicator holder (6). The applicator holder (6) is configured for partially containing the applicator (7) at its most proximal side, with respect to the proximal part of the pen. The front housing (10) is configured for partially containing the applicator holder (6) and the valve housing (3). Back housing (1), valve housing (3), perforator holder (4), applicator holder (6) and front housing (10) are preferably made of polymers and fabricated by injection moulding in a mould. Back housing (1), valve housing (3), perforator holder (4), applicator holder (6) and front housing (10) are preferably made of styrene acrylonitrile.

Figure 2:
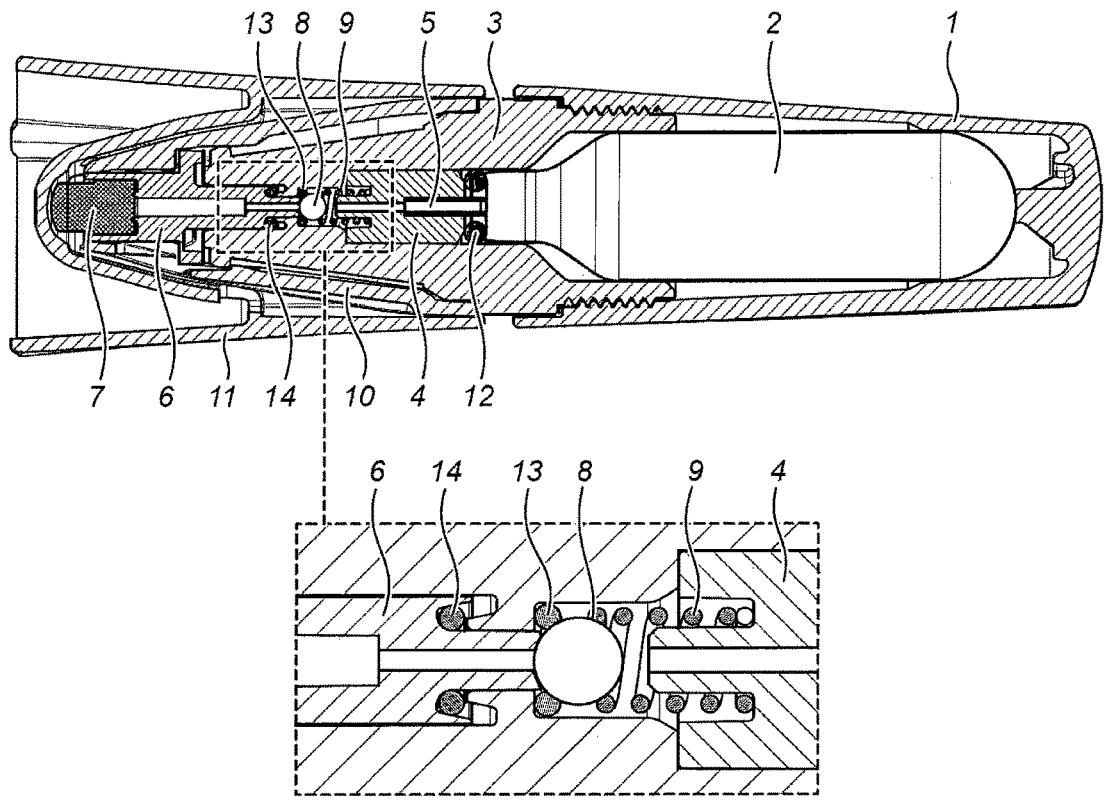
FIG. 2 is a cross-sectional view in the longitudinal direction of a possible embodiment of a pen according to the present invention in a rest position.

FIG. 2 is a cross-sectional view in the longitudinal direction of a possible embodiment of a pen according to the present invention, in which the pen is in a rest position. Rest position means that no flow of coolant is possible up to the applicator (7). In this possible embodiment, the coolant passage is present as a central opening that extends axially over the proximal part of the pen. In particular, the coolant passage is realised as a combination of the following components, from the distal part to the proximal part of the pen, placed in coolant communication to each other: an opening of the perforator (5), an opening of the perforator holder (4), an opening at the valve body, in which the spring (9) and ball (8) are located, and an opening in the applicator holder (6). In FIG. 2, the gas cartridge (2) comprising coolant is discharged under increased pressure. The term "discharged" means that the coolant can escape from the holder through an opening. This opening in the gas cartridge (2) is created by puncturing the closure of the gas cartridge (2) by the perforator (5). Via the perforator (5), the coolant can flow to the volume of the valve body. In the valve body, the part of the coolant passage from the valve body to the applicator holder (5) is closed off by the ball (8) of the valve body. The bearing of the ball (8) in the spring (9) ensures the ball (8) is positioned against the applicator holder (6), so that the opening of the latter is blocked or closed off. The pressure that is exercised by the coolant also contributes to the positioning of the ball (8).

Figure 3:
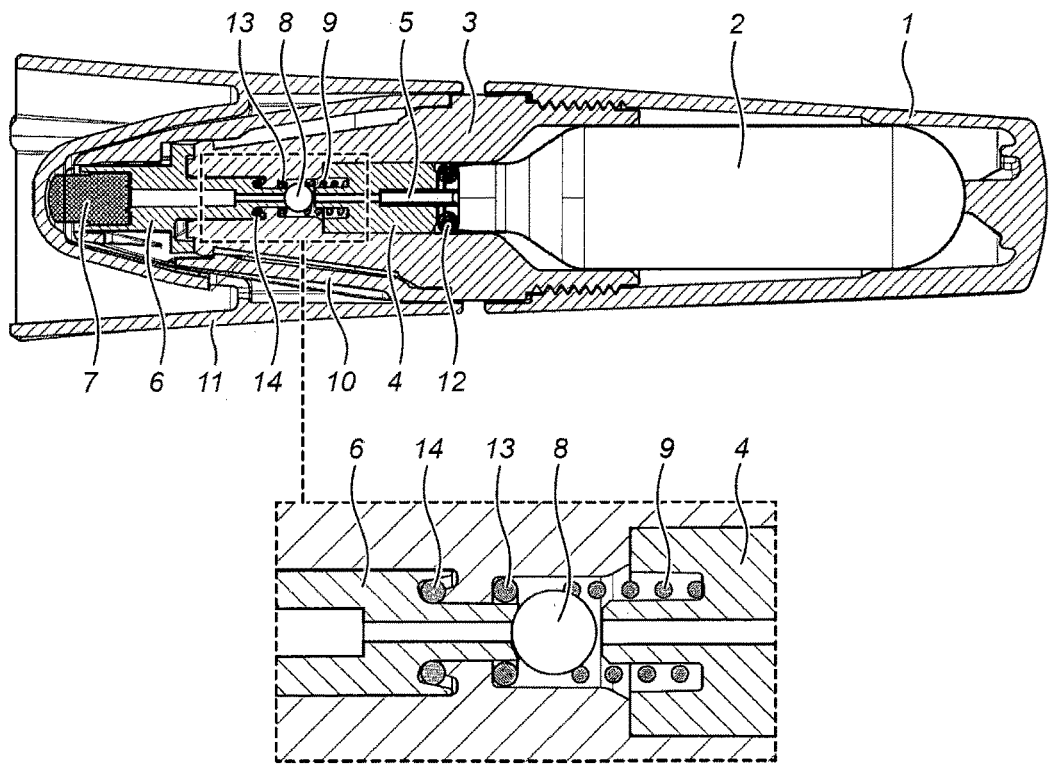
FIG. 3 is a cross-sectional view in the longitudinal direction a possible embodiment of a pen according to the present invention in an activated position.
Figure 4:
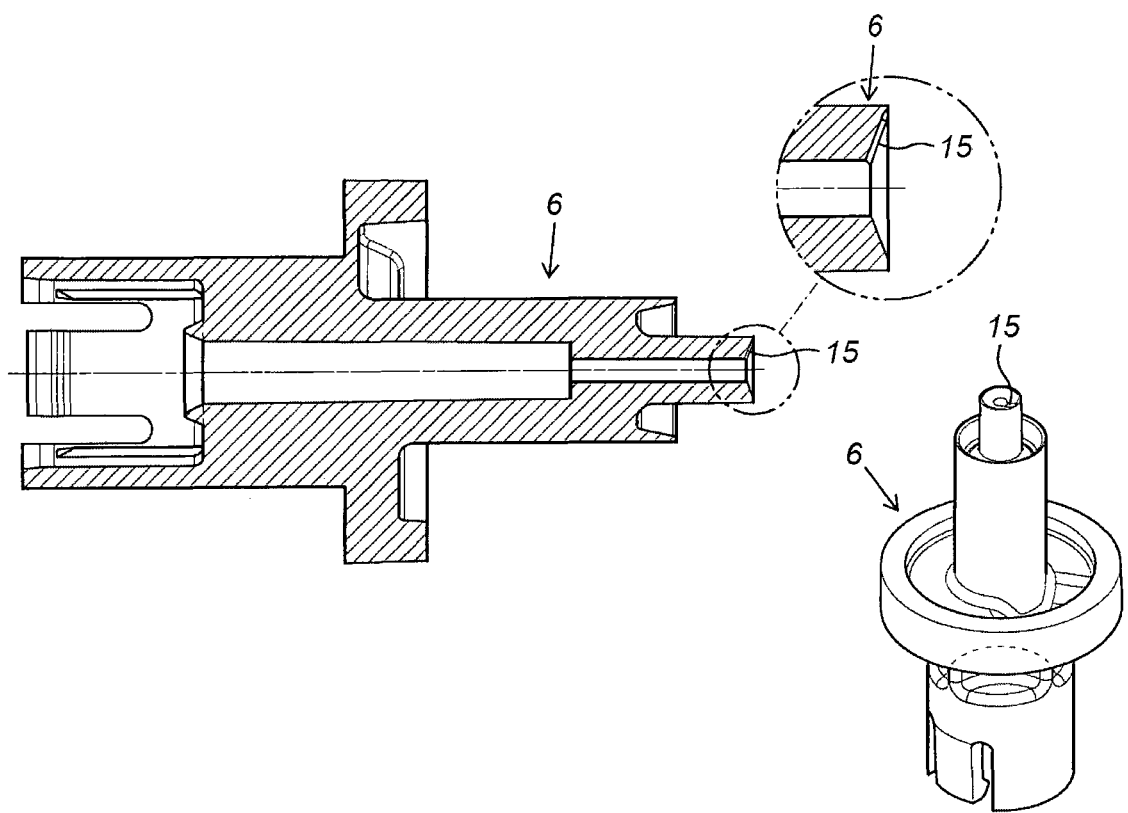
FIG. 4 shows a cross-sectional view in the longitudinal direction of a possible embodiment of an applicator holder, with enlargement of a bypass in the applicator holder, next to a three-dimensional view of a possible embodiment of the applicator holder, according to the present invention.

FIG. 3 is a cross-sectional view in the longitudinal direction of a possible embodiment of a pen according to the present invention, in which the pen is in an activated position. Activate position means that a flow of coolant is possible up to the applicator (7). This activated position is reached by exercising an external pressure onto the proximal part of the pen, in which this external pressure is directed against the internal pressure caused by the coolant in the pen, and directed against the force of the spring (9). The spring (9) contributes to allowing the ball (8) to keep its position with respect to the axis of the spring (9) when exercising the external pressure. In this possible embodiment, exercising the external pressure will enable the ball (8) to be pushed against the spring (9) via the applicator holder (6) that is moved in the direction of the distal part of the pen. As a result, the volume taken by the ball (8) and spring (9) is reduced, as a result of which the pressure will locally increase. The increase of the pressure in the pen allow the coolant to be moved past the valve body via a bypass that is located at a distal side, seen from the proximal and distal part of the pen, of the applicator holder (6). In other words, the bypass in the coolant passage is provided at the applicator holder (6). A possible embodiment of an applicator holder (6) provided with a bypass (15) is shown in FIG. 4. At the distal side of the applicator holder (6), a concave seat is present against which the ball (8) of the valve body can placed. In this concave seat, a notch is radially cut, which notch is a possible embodiment of the bypass (15). The notch starts at the outer periphery of the distal side of the applicator holder (6) and ends in a discharge of the opening of the applicator holder (6), at the distal side of the latter. The diameter of the bypass (15) is significantly smaller than the diameter of the coolant passage. Moreover, the embodiment of the bypass as shown in FIG. 4 is placed in an angle of 67.5° with respect to the axially extending coolant passage. The orientation and design of the bypass (15) allow coolant, in the activated position, to flow past the bypass (15) to the part of the coolant passage delimitated by the applicator holder (6) en subsequently in the direction of the applicator (7). Therefore, the coolant can reach the applicator (7) in the activated position. The flow of coolant past the bypass (15) allows to regulate the velocity of the coolant. Moreover, when entering the bypass (15) to the coolant passage, the coolant experiences a velocity increase, because of the increase in the available volume. In both FIG. 2 and FIG. 3, a closing cap (11) is mounted onto the proximal part of the possible embodiment of the pen. In rest position of the pen, the closing cap (11) protects the applicator (7). In activated position of the pen, closing off the applicator (7) in a liquid-tight manner by means of the closing cap (11) allows as much liquid coolant as possible to be used for evaporative cooling at the applicator (7). When the applicator (7) has been sufficiently cooled down to low temperatures by means of evaporative cooling, the closing cap (11) can be removed from the proximal part of the pen so that this applicator (7) can be used for treating dermatological disorders. It should be remarked that the applicator holder (6) protects the applicator (7) except for the surface of the applicator (7) in close proximity of the administration surface. Loss of cold via the non-functional part of the applicator (7), that is the part of the applicator (7) that is not brought into contact with the surface to treat, is avoided in this way.

Figure 5:
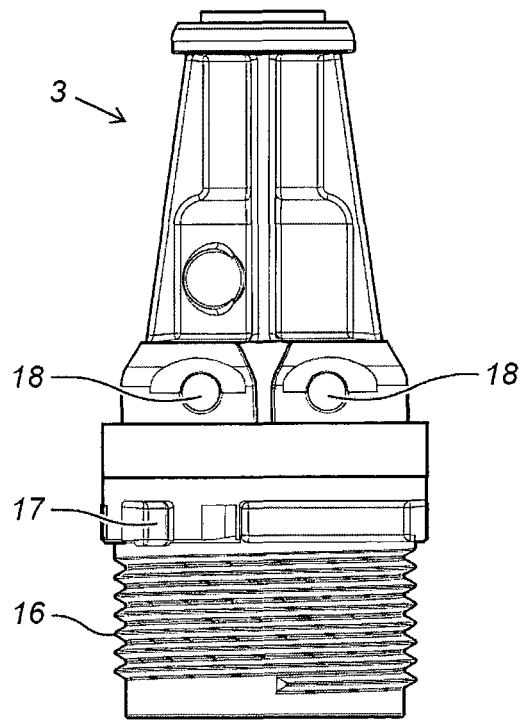
FIG. 5 is a side view of a possible embodiment of a valve housing according to the present invention.

FIG. 5 is a side view of a possible embodiment of a valve housing (3) according to the present invention. FIG. 6 shows a cross-sectional view in the longitudinal direction of a possible embodiment of a back housing (1), next to a three-dimensional view of a possible embodiment of the back housing (1), according to the present invention. The combination of FIG. 5 and FIG. 6 shows a clear view of a possible mechanism by means of which valve housing (3) and back housing (1) can be attached to each other. The valve housing (3) has a thread (16). The back housing (1) also has a thread (19). Next to the thread (19), the back housing (1) show a toothed pattern (20). At the valve housing (3), a projecting structure (17) is present next to the thread (16), which projecting structure (17) has limited dimensions compared to the diameter of the valve housing (3). Both threads can be brought into each other by means of a turning movement. By tightening the thread (16) of the valve housing (3) in the thread (19) of the back housing (1), the projecting structure (17) of the valve housing (3) will be brought at the toothed pattern (20) of the back housing (1). The toothed pattern (20) blocks a movement of the projecting structure (17) in the turning direction for loosening, as a result of which loosening of the valve housing (3) with respect to the back housing (1) is avoided. In the cross-sections in the longitudinal direction of a possible embodiment of a pen, shown in FIG. 2 and FIG. 3, the proximal part of the pen is connected to the distal part of the pen by means of the attachment of valve housing (3) and back housing (1). Considering the presence and position of the perforator (5) in the proximal part of the pen, when attaching the proximal part of the pen to the distal part of the pen, by means of the turning movement, the perforator (5) will puncture a present closure of the holder (2) so that coolant can be released in the proximal part of the pen. When the proximal part and the distal part of such an embodiment are provided separately, a user can attach both parts to each other by means of the turning movement. The advantage is that the coolant can only be released just before a user wants to use the pen. The advantage is that losses of coolant during storage are limited. The protection against loosening the valve housing (3) with respect to the back housing (1) once these have been tightened, is important for the safety of a user of the pen. Loosening the valve housing (3) with respect to the back housing (1), once the coolant has been released, is in effect dangerous, since the coolant under increased pressure would be released to the environment in an uncontrolled manner. In FIG. 5, ventilation openings (18) of the valve housing (1) for the discharge of gaseous coolant are also shown. They are important for avoiding an overpressure in the pen as a result of the accumulation of gaseous coolant. Moreover, in FIG. 6, the rounded corners (21) of a triangular embodiment of the back housing (1) is shown. The advantage of this triangular shape of the back housing (1) is that, when the back housing (1) or the pen is located on a horizontal surface, it can start rolling over this surface when a user comes into contact, for example when a force is exercised. Compared to non-rounded corners, the advantage of the rounded corners (21) of the embodiment of the back housing (1) is that the risk of rupture, for example if the back housing (1) or the pen falls onto a surface, is smaller.

FIG. 7 is a cross-sectional view of a possible embodiment of a closing cap (11) according to the present invention. FIG. 8 shows a possible embodiment of a front housing (10) according to the present invention. The combination of these two figures shows a clear view of a safety measure that prevents unintentional positioning of the closing cap (11) onto the proximal part of the pen, as well as the possible resulting unintentional positioning of the pen in the activated position. This safety measure relates to projections (22) of the closing cap (11) that should be placed in corresponding recesses (24) of the front housing (10), before an external pressure on the closing cap (11) can lead to a positioning of the pen in the activated position. The shown embodiments of the closing cap (11) show three projections (22) that can be positioned in the corresponding three recesses (24) of the shown embodiment of the front housing (10). Only one of these recesses (24) is clearly shown in FIG. 8. The recesses (24) of the front housing (10) moreover also function as ventilation openings to evacuate gaseous coolant. The embodiment of the closing (11) has several ventilation openings (23).

The front housing (10) can be provided with a colour that changes depending on the temperature. By means of a change in colour, it can thus be indicated to a user when the applicator (7) has been cooled down sufficiently to start a treatment of dermatological disorders. Inversely, it can be indicated when the applicator (7) is not cold enough or cannot sufficiently be cooled down anymore to start a treatment. The polymer material of the front housing (10) can therefore be covered with a temperature-sensitive or thermochromic dye that turns colour when the applicator (7) reaches a sufficiently cold temperature. In addition, when fabricating the front housing (10), the polymer material can be mixed with such a thermochromic dye, in which preferably a homogeneous coloured front housing (10) is obtained. The change in colour is obtained by exceeding a particular temperature value. Any thermochromic dye for obtaining a colour change at a particular temperature value, as known in the state of the art, can be used. A colour change can for example be obtained by exceeding a temperature of −70° C. In an analogous way, the closing cap (11) can be provided with a thermochromic dye to indicate whether or not the applicator (7) has been cooled down sufficiently to start a treatment of dermatological disorders.

In a third aspect, the invention provides the use of a pen according to an embodiment of the invention in the treatment of warts.

Hence, to this aspect, the following method is associated. A method for the administration of a wart pen, which method comprises the following steps:
putting at disposal a wart pen appropriate for the treatment of warts, in which the cart pen comprises:
a cartridge housing 1 in which a gas cartridge 2 is placed at least temporarily, which gas cartridge 2 contains a coolant under increased pressure;
a dose-measuring device with a coolant, which dose-measuring device is appropriate for being attached at a distal side to a cartridge housing 1, which dose-measuring device is equipped at a proximal side with an applicator 7 provided with an administration surface for administrating low temperatures to one or more warts to treat, which dose-measuring device comprises distally to the applicator 7 a perforator 5 which is arranged for puncturing the gas cartridge 2 and which dose-measuring device is provided between the applicator 7 and the perforator 5 with a valve body for closing off and/or opening the coolant passage;
a closing cap 11 appropriate for being positioned in a removable manner at or being attached to the proximal side of the dose-measuring device;
administering the valve body;
optionally, using the applicator 7 at one or more warts;
at which for administering the valve body, the closing cape 11 is attached to the proximal side of the dose-measuring device, and the closing cap 11 is removed after administering the valve body.

For possible embodiments of a wart pen that can be used in the method according to the second aspect of the present invention, we refer to the description of the wart pen according to the first aspect of the present invention.

In a step of the method, a wart pen is put at disposal, in which coolant from the gas cartridge 2 is available for the dose-measuring device. A next step of the method involve the administration of the valve body. In unused condition of the wart pen, the valve body is preferably closed. When administering the valve body, the valve body is opened so that coolant can flow to the applicator 7, which applicator is subsequently cooled down. After administering the valve body for a while, the applicator 7 is used at one or more warts for treatment thereof. In the method for administering the valve body, the closing cap 11 is attached to the proximal side of the dose-measuring device, and after administering the valve body, the closing cap 11 is removed. This means that when administering the valve body, the closing cap 11 is positioned onto and attached to the proximal side of the dose-measuring device. The attachment of the closing cap 11 to the proximal side of the dose-measuring device protects the applicator 7 from the environment. This protection of the applicator 7 comprises both the liquid-tight enclosure of the applicator 7 and the isolation of the applicator 7 with respect to the environment. As a result, when administering the valve body, the applicator 7 can be cooled down quicker by evaporative cooling of the coolant at the applicator 7 than when the closing cap 11 would not be attached to the proximal side of the dose-measuring device. This quicker and consequently more efficient cooling down of the applicator 7 entails a saving of coolant, which is economically advantageous for a user of the wart pen.

According to an embodiment of the second aspect of the invention, the method further comprises the step of puncturing the gas cartridge 2 by means of the perforator 5. Adding this step to the method enables a user, just before using the wart pen, to create an opening in the gas cartridge 2, so that the coolant can be released out of the gas cartridge 2 to the dose-measuring device. The advantage is that the gas cartridge 2 can be closed off until the first use of the wart pen, which prevents possible loss of coolant before using the wart pen.

According to an embodiment of the second aspect of the invention, a force of maximum 750 N is exercised for puncturing the gas cartridge 2 by means of the perforator 5. For puncturing the gas cartridge 2 by means of the perforator 5, a force of maximum 600 N is preferably exercised, and more preferably a force of maximum 450 N. The puncturing of the gas cartridge 2 by means of the perforator 5 as a result of forces corresponding to the above-mentioned forces contributes to a safe discharge of coolant by puncturing the gas cartridge 2 with reasonable force, without causing significant damage to a perforator 5, cartridge housing 1 or dose-measuring device. The perforator 5, cartridge holder 1 and dose-measuring device are preferably shaped in such way and preferably fabricated of sufficiently strong materials, that they can resist the above-mentioned forces. For example, the perforator 5 is made of metal. The cartridge housing 1 and dose-measuring device are for example made of a synthetic material. The cartridge housing 1 and/or at least a part of the dose-measuring device are preferably made of a synthetic material reinforced with glass fibres or of a synthetic material reinforced with analogous appropriate components for reinforcement.

According to an embodiment of the second aspect of the invention, the administration surface of the applicator 7 reaches a temperature as a result of the administration of the valve body that is lower than the temperature of the coolant. The administration surface of the applicator 7 is the surface of the applicator 7 by which low temperatures can be administered to one or more warts to treat. The temperature that is lower than the temperature of the coolant is reached by evaporative cooling, namely because heat is withdrawn from the applicator 7 for the evaporation of liquid coolant. The applicator 7 preferably has a porous structure and is preferably constituted of a material with a high thermal conductivity and is configured to spread liquid coolant. The porous structures contains pores. Through the applicator 7, a central axis in the direction of the administration surface can be considered. Across the volume of the applicator 7, the average pore size per surface can vary transverse to this central axis. The average pore size per surface transverse to this central axis in the direction of the administration surface preferably decreases. As a result, there is less room for discharging the gas that has been generated at the evaporative cooling at the administration surface, which locally results in an increased cooling. Sufficient isolation of the applicator 7 with respect to the environment can contribute to achieving a temperature of the administration surface of the applicator 7 that is lower than the temperature of the coolant, by evaporative cooling of the applicator 7.

According to an embodiment of the second aspect of the invention, dinitrogen oxide or $N_2O$ is used as a coolant. $N_2O$ has a boiling point of −89° C. and will be able to withdraw much heat from the applicator 7 as a result of evaporation, so that the applicator can be cooled down sufficiently for a wart treatment, preferably a temperature lower than −60° C., more preferably a temperature lower than −70° C. and most preferably a temperature lower than −75° C.

According to an embodiment of the second aspect of the invention, the administration surface of the applicator 7 reaches a temperature of −80° C. to −95° C. by administering the valve body when $N_2O$ is used as a coolant. The specific reached temperature is amongst other things dependent on the structure of the applicator 7 and the degree of protection of the applicator 7 by the closing cap 11 when administering the valve body. The above-mentioned temperatures are appropriate as starting temperatures for the treatment of warts.

According to an embodiment of the second aspect of the invention, the valve body is administered for a period of 0.2 s to 0.5 s. Since the applicator 7 is protected from the environment by means of the closing cap 11 when administering the valve body in the method, the administration surface of the applicator 7 can already be cooled down by means of $N_2O$ to a temperature of −80° C. to −95° C. by administering the valve body for such a short period of time.

In a preferred embodiment, said method is a method for the administration of a wart pen, which method comprises the following steps:
  putting at disposal a wart pen appropriate for the treatment of warts, in which the cart pen comprises:
    a cartridge housing (1) in which a gas cartridge (2) is placed at least temporarily, which gas cartridge (2) contains a coolant under increased pressure;
    a dose-measuring device with a coolant, which dose-measuring device is appropriate for being attached at a distal side to a cartridge housing (1), which dose-measuring device is equipped at a proximal side with an applicator (7) provided with an administration surface for administrating low temperatures to one or more warts to treat, which dose-measuring device comprises distally to the applicator (7) a perforator (5) which is arranged for puncturing the gas cartridge (2) and which dose-measuring device is provided between the applicator (7) and the perforator (5) with a valve body for closing off and/or opening the coolant passage;
    a closing cap (11) appropriate for being positioned in a removable manner at or being attached to the proximal side of the dose-measuring device;
  administering the valve body;
  optionally, using the applicator (7) at one or more warts;
  at which for administering the valve body, the closing cap (11) is attached to the proximal side of the dose-measuring device, and the closing cap (11) is removed after administering the valve body, and this method is extended with, one, several or each of the following options:
    the method further comprises the puncturing of the gas cartridge (2) by means of the perforator (5);
    for puncturing the gas cartridge (2) by means of the perforator (5), a force of maximum 750 N is exercised;
    by administering the valve body, the administration surface of the applicator (7) reaches a temperature that is lower than the temperature of the coolant;
    dinitrogen oxide is used as a coolant;
    the administration surface of the applicator (7) reaches a temperature of −80° C. to −95° C. by administering the valve body; and/or
    the valve body is administered during a period of time of 0.2 s to 5.0 s.

In the following, the invention will be described by means of a non-limiting example illustrating the invention, and that is not meant to be interpreted as limiting the scope of the invention.

EXAMPLE 1

FIG. 1 up to and including 8 illustrate a possible embodiment of a wart pen according to the present invention. According to this possible embodiment, the applicator 7 is carried by housing 6, the perforator 6 is enclosed by a housing 4 and the valve body has the shape of a ball 8 resiliently carried by a spring 9. According to this possible embodiment, the dose-measuring device furthermore contains two housings 3, 10 for containing components of the dose-measuring device. O-rings 12, 13, 14 are present to avoid losses of coolant.

In FIG. 2, the wart pen is shown, in which coolant from the gas cartridge 2 can flow through the dose-measuring device up to the valve body. In FIG. 2, the valve body can in effect be closed off and the coolant can flow up to the ball 8 of the valve body. The opening of the gas cartridge 2, where coolant can flow in the direction of the dose-measuring device, is preferably cause by puncturing the gas cartridge 2 by means of the perforator 5. FIG. 3 shows the wart pen, in which the valve body is administered. The administration of the valve body is obtained by exercising an external pressure onto the wart pen, in which this external pressure is directed against the internal pressure caused by the coolant in the wart pen, and directed against the force of the spring 9. By administering the valve body, the coolant will be able to flow to the applicator 7.

Flow control of the coolant of the valve body to the applicator 7 is regulated by leading the coolant past a narrowing 15 that is present in the housing 6 of the applicator 7. As shown in FIG. 4, the side of the related housing 6 adjoining the ball 8 is concave. The narrowing 15 is realized as a notch in this concave shape adjoining the ball 8. The narrowing 15 is connected to the part of the coolant passage that is delimited by the housing 6 of the applicator.

In the possible embodiment of the wart pen, the dose-measuring device and the cartridge housing 1 are attached to each other via a turning movement in a particular turning direction, in which the thread 16 of a housing 2 of the dose-measuring device can be tightened into the thread 19 of the cartridge housing 1 and in which the projecting structure 17 of the housing 3 of the dose-measuring device will eventually be brought at the toothed pattern 20 of the cartridge housing 1. The toothed pattern 20 blocks a movement of the projecting structure 17 in the turning direction opposite to the turning movement for tightening, as a result of which loosening of the valve housing 3) with respect to the cartridge housing 1 is avoided. Considering the presence and position of the perforator 5 in the dose-measuring device, when attaching the dose-measuring device to the cartridge housing 1 by means of the turning movement, the perforator 5 will puncture a still enclosed gas cartridge 2 so that the coolant is released to the dose-measuring device. The protection against loosening once the dose-measuring device and cartridge housing 1 have been tightened, is important for the safety of a user of the pen. In effect, loosening is dangerous, since the coolant under increased pressure can be released to the environment in a uncontrolled manner.

The possible embodiment of the wart pen contains a safety measure avoiding unintentional positioning and attachment of the closing cap 11 at the proximal side of the dose-measuring device, as well as possible resulting administration of the valve mechanism of the wart pen. This safety measure relates to projections 22 of the closing cap 11 that should be placed in corresponding recesses 24 of the housing 10 of the dose-measuring device, before an external pressure on the closing cap 11 can lead to an administration of the valve body. The shown embodiment of the closing cap 11 shows three projections 22 that can be positioned in the corresponding three recesses 24 of the shown embodiment of the related housing 10. Only one of these recesses 24 is clearly shown in FIG. 8. The recesses 24 of the related housing 10 moreover also function as ventilation openings to evacuate gaseous coolant. The embodiment of the closing 11 has several ventilation openings 23. Moreover, another housing 3 of the dose-measuring device also contains ventilation openings 18.

In the possible embodiment of the wart pen, the cartridge housing 1 has a triangular shape with rounded corners. The advantage of the shape of the cartridge housing 1 is that, when the cartridge housing 1 or the wart pen is located on a horizontal surface, it can start rolling over this surface when a user comes into contact, for example when a force is exercised. Compared to non-rounded corners, the advantage of the rounded corners 21 of the preferred embodiment of the cartridge housing 1 is that the risk of rupture, for example if the cartridge housing 1 or the wart pen falls onto a surface, is smaller.

Figure 13:
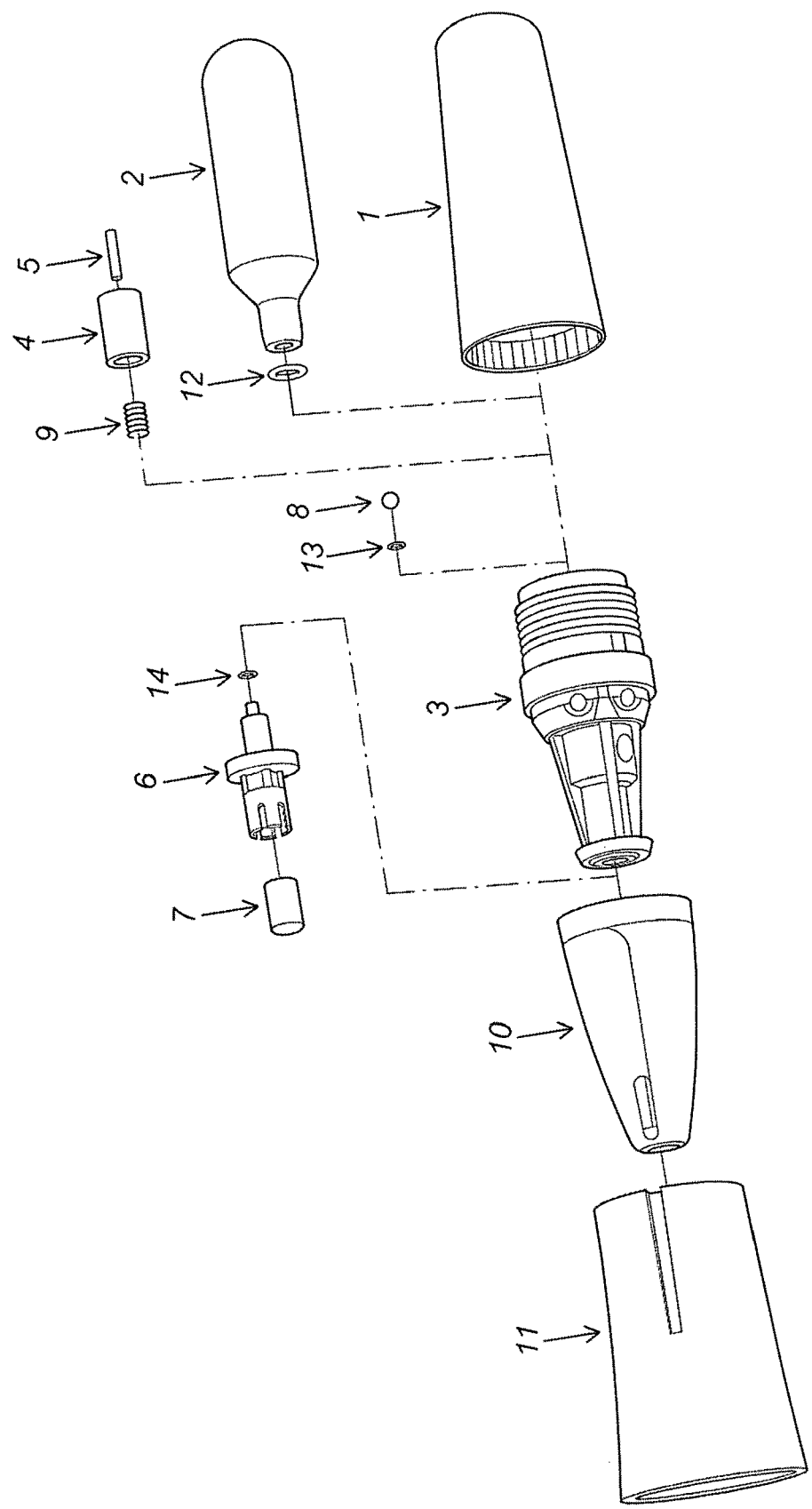
FIG. 13 is an exploded view of a possible embodiment of a pen according to the present invention, wherein the applicator is made of a PU-foam.
Figure 14:
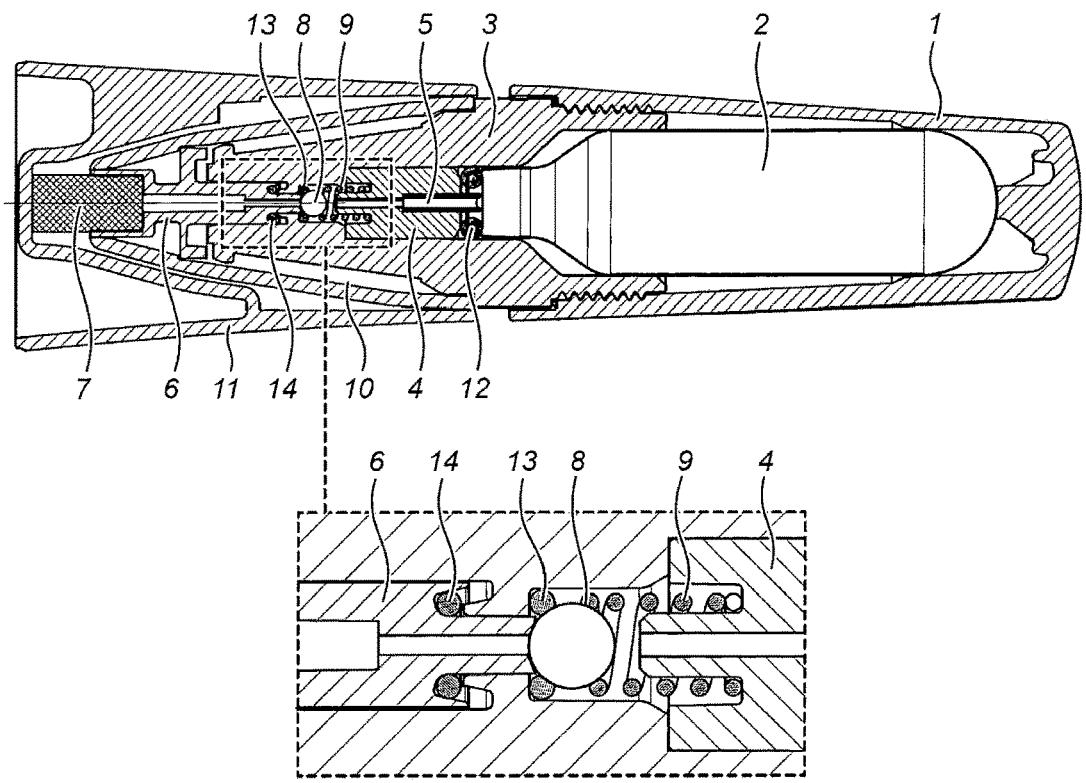
FIG. 14 is a cross-sectional view in the longitudinal direction of a possible embodiment of a pen according to the present invention in a rest position, wherein the applicator is made of a PU-foam.
Figure 15:
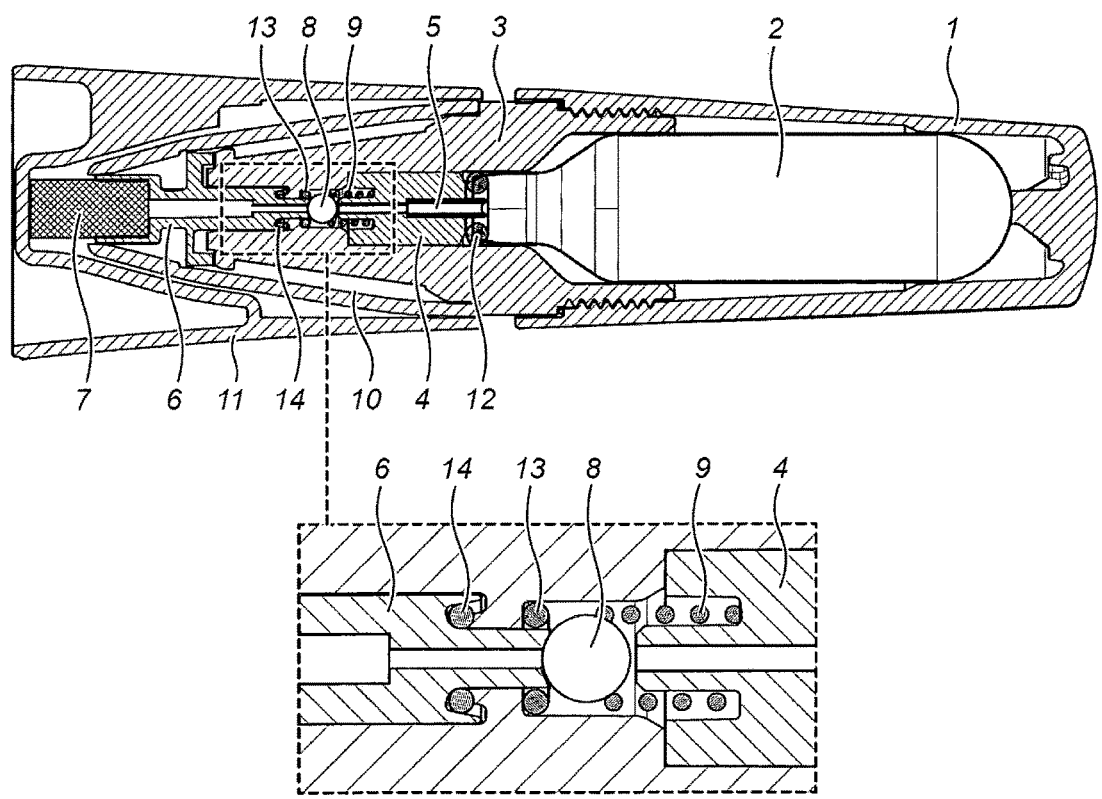
FIG. 15 is a cross-sectional view in the longitudinal direction a possible embodiment of a pen according to the present invention in an activated position, wherein the applicator is made of a PU-foam.

FIG. 13 up to and including 15 represent a possible alternative embodiment of the invention, wherein the applicator 7 is made in a transformable polyurethane-foam. As a result, also the shape of the closing cap 11 has been adapted to the longer cylindrical applicator 7. The closing cap 11 close to the most tight around the applicator tip or the administration surface, hampering the flow of coolant around the applicator tip or administration surface. As a result, the greatest cooling effect happens around the applicator tip or the administration surface, and that is the place where the lowest temperature is maintained for the longest time.

EXAMPLE 2

As described above, the present invention relates to a compact pen, especially for home use, that can, by means of evaporative cooling, reach temperatures at an applicator that are sufficiently low for the treatment of dermatological disorders, without causing hypothermia and/or without undesired interaction of the low temperatures with areas that do not require treatment, such as, for example, healthy skin tissue surrounding a dermatological disorder. Moreover, a pen according to the present invention can maintain these low temperature for a sufficiently long period of time for the efficient treatment of dermatological disorders. For a possible embodiment of a wart pen according to the present invention, an experiment has been conducted to verify which temperatures can be reached at the administration surface of the applicator 7 by means of evaporative cooling of the applicator 7. The wart pen corresponds to the possible embodiment as shown in FIGS. 1 to 8.

Moreover, the evolution of the reached temperature in function of the time is verified. For example, in effect, for warts, low temperatures, lower than −50° C., have to be reached for an effective treatment of the warts. These low temperatures should also be maintained for a sufficiently long period of time. For the treatment of ordinary warts, a treatment period of 20 s at these low temperatures is in effect recommended. For foot warts, after this treatment period of 20 s, an additional treatment period of 20 s desired, in which the temperatures remain lower than −25°, because of the thick epidermis of feet. A wart pen according to the present invention can reach these time and temperature conditions at the administration surface of an applicator 7, as shown in the experiment for embodiments of the wart pen. During the experiment, in particular the effect of different applicator 7 types on the temperature reached by evaporative cooling was verified. Four cylindrical applicator 7 types were evaluated, that is three single-layer applicators, each composed of a hydrophobic porous material, and a double-layer applicator, composed of an accumulation of hydrophobic porous materials used for the single-layer applicators. A first single-layer applicator was made of a first hydrophobic porous material with an average pore size varying from 20 to 40 μm and a porosity higher than 40%. A second single-layer applicator was made of a second hydrophobic porous material with an average pore size varying from 80 to 120 μm and a porosity higher than 35%. The third single-layer applicator was a polyurethane foam with an average pore size of 400 to 700 μm. The fourth applicator was a double-layer applicator made of an accumulation of the hydrophobic porous materials used for the single-layer applicators.

For the double-layer applicator, the first hydrophobic porous material was located at the administration surface, while the second hydrophobic material was further located from the administration surface. For the double-layer applicator, the first hydrophobic porous material amounted to about 5% to 60% of the total volume of the double-layer applicator. Three of the cylindrical applicator had the following dimensions: a total length of 10.00±0.35 mm, along the central longitudinal axis through the applicator, in which the upper and largest part, with a diameter of 6.40±0.15 mm, had a length of 5.00±0.25 mm. The lower and also smallest part had a diameter of 5.80±0.15 mm. The administration surface was located at the smallest part. The upper surface of the free end of the smallest part, corresponding to the administration surface, was convex. This convex shape was characterised by a radius of 5.50 mm, measured from the centre of the area connecting the upper and lower part. The forth applicator that was made from polyurethane foam has a simple cylindrical geometry with a diameter of 7±0.6 mm and a length of 13.5±1 mm.

In the experiment, liquid $N_2O$ under increased pressure was used as a coolant under increased pressure. This coolant was present in a gas cartridge 2 with an opening, in which the opening was initially closed off by means of a closure. In a first step, the coolant was released by puncturing the closure by means of a perforator 5 of the wart pen. After releasing the coolant, the coolant could flow up to the valve body of the wart pen. Subsequently, during a period of time of about 1 s, an external pressure was exercised on the wart pen for the administration of the valve body, which external pressure was exercised in opposite direction to the pressure exercised by the coolant. More in particular, the external pressure was exercised on a removable closing cap 11 that is mounted at the proximal side of the dose-measuring device. While exercising the external pressure, the coolant could flow past the valve body to an applicator 7, as a result of which the applicator 7 was cooled down by means of evaporative cooling. The cooling down of the applicator 7 according to the above-mentioned steps was considered as a "dose" in the experiment. Immediately after exercising the external pressure, the removable closing cap 11 of the cart pen was removed and the administration surface of the applicator 7 was immediately placed onto a thermometer to determine immediately the temperature of the administration surface.

Figure 9:
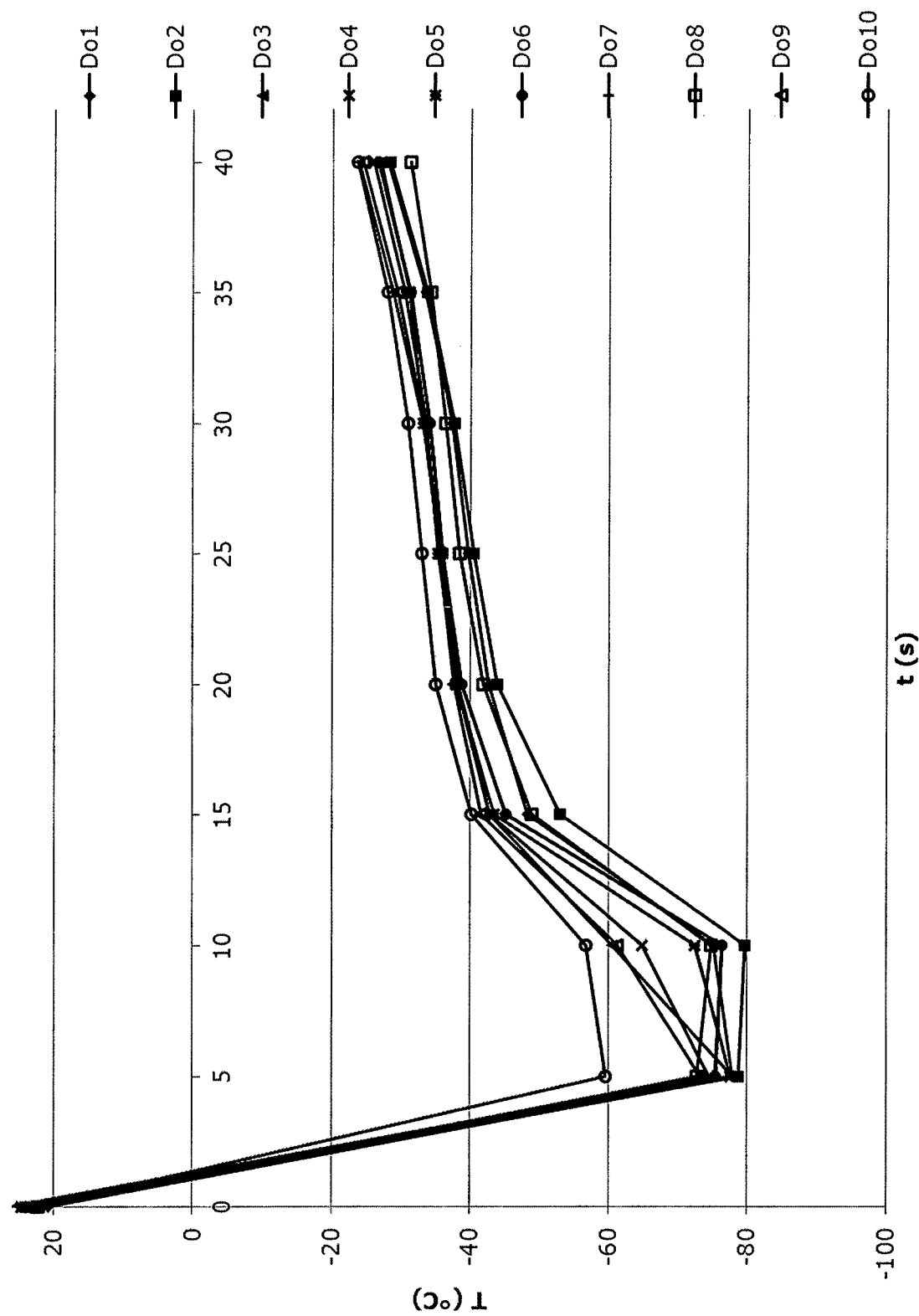
FIG. 9 shows a graph of the temperature versus the time for experiments using possible embodiments of a pen according to the present invention.
Figure 10:
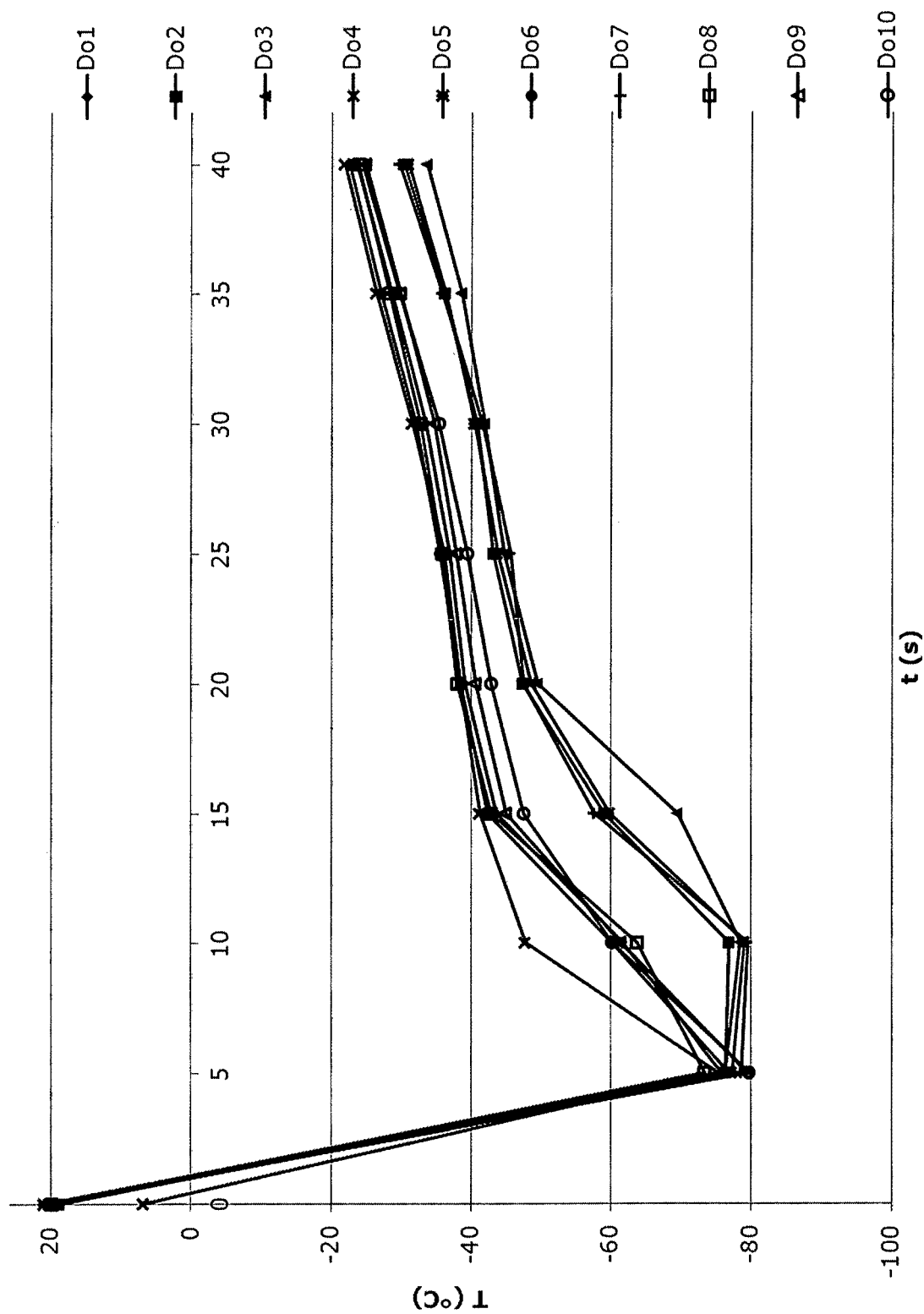
FIG. 10 shows a graph of the temperature versus the time for experiments using possible embodiments of a pen according to the present invention.
Figure 11:
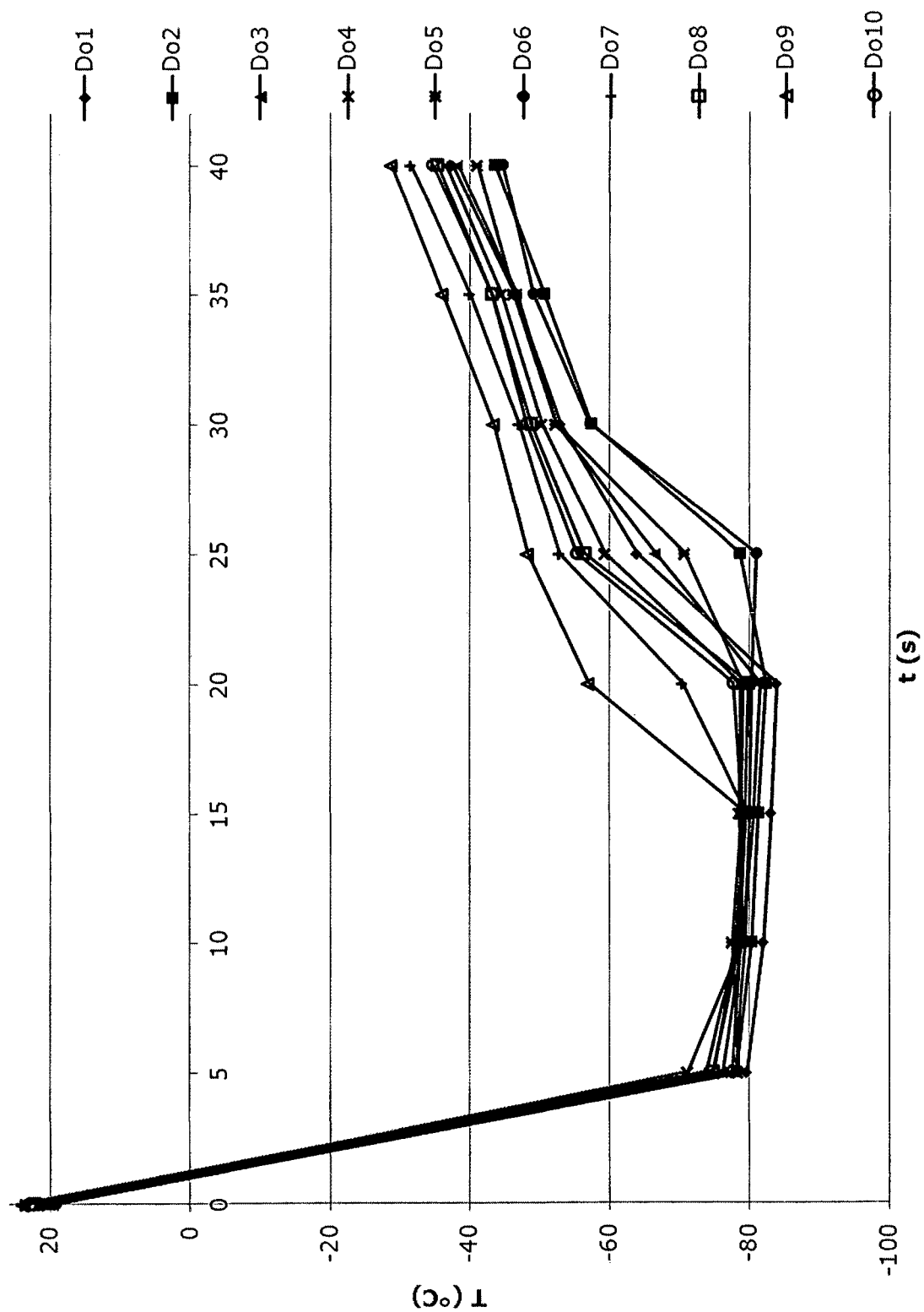
FIG. 11 shows a graph of the temperature versus the time for experiments using possible embodiments of a pen according to the present invention.
Figure 12:
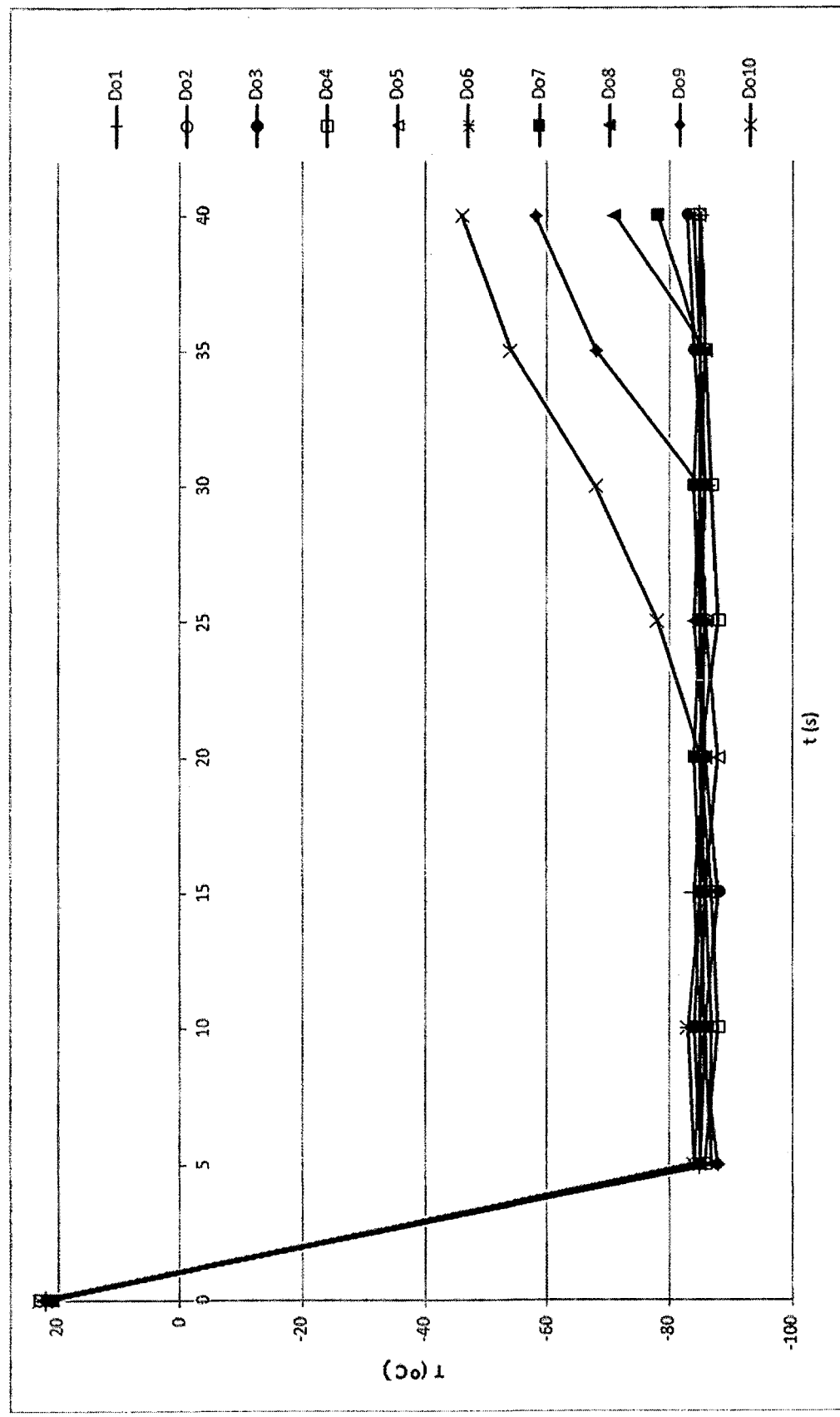
FIG. 12 shows a graph of the temperature versus the time for experiments using possible embodiments of a pen according to the present invention.

At the experiment, 10 doses were followed for each type of applicator. FIGS. 9-12 show for 10 doses (respectively called "Do1", "Do2", "Do3", "Do4", "Do5", "Do6", "Do7", "Do8", "Do9" and "Do10") per type of applicator detailed data of the temperature (T) in function of the time (t) (0 to 40 s, with an interval of 5 s). FIG. 9 shows the data for the first single-layer applicator. FIG. 10 shows the data for the second single-layer applicator. FIG. 11 shows the data for the double-layer applicator. FIG. 12 shows the data for the single-layer applicator made out of polyurethane foam.

Differences in change of temperature in function on the time were observed for the single-layer applicators with respect to the double-layer applicator. For the single-layer applicators, two approximately linear segments could be observed, one of 5 to 15 s and one of 15 to 40 s. The increase in temperatures increases quickly from 5 to 15 s. From 15 to 40 s, the increase in temperature was clearly slower. The double-layer applicator showed a different temperature curve compared to the single-layer applicators, beginning with a lag phase (5 to 15 s) followed by an approximately linear temperature increase in function of the time. During the lag phase, the average temperature remained lower than −71° C., after which an approximately linear increase in temperature was observed between 15 s and 40 s. It could be observed that from 15 s, the measured temperatures was significantly lower for the double-layer applicator compared to the single-layer applicators. The double-layer applicator can maintain the cold obtained from evaporative cooling longer than the single-layer materials and is thus extremely appropriate for the treatment, by means of low temperatures, of warts. With the single-layer applicator made out in polyurethane-foam, an average temperature of lower than 85° C., (5 to 25 s) is maintained considerably longer than observed for the other applicators (5 to 15 s).

What is claimed is:

1. A pen for the treatment of dermatological disorders by means of a coolant, the pen comprising: a distal part comprising a holder for storage of the coolant; and a proximal part axially aligned with the distal part and comprising: an applicator for the administration of the coolant to a dermatological surface; and an applicator holder to which the applicator is mounted; a coolant passage extending axially through portions of the distal and proximal parts to communicate the coolant from the holder to the applicator; a ball biased against a distal end of the applicator holder and occluding the coolant passage when the pen is in a rest position and an activated position; and a bypass comprising a radially extending channel defined in the distal end of the applicator holder and in fluid communication with the coolant passage, wherein the coolant is prevented from flowing through the coolant passage to the applicator when the pen is in the rest position, wherein the coolant is allowed to flow through the coolant passage to the applicator via the bypass when the pen is moved to the activated position, and wherein the applicator comprises an administration surface, and an average pore size of the applicator decreases in the axial direction towards the administration surface.

2. The pen according to claim 1, wherein the diameter of the bypass is smaller than the diameter of the coolant passage.

3. The pen according to claim 1, wherein the applicator comprises a transformable foam.

4. The pen according to claim 3, wherein said foam has a hardness of 4 to 30 kPa.

5. The pen according to claim 1, wherein the applicator has a density of 19 to 67 kg/m3.

6. The pen according to claim 1, wherein the average pore size of the applicator decreases from 60-250 μm to 0.1-55 μm.

7. The pen according to claim 1, wherein the proximal part of the pen further comprises a perforator located between the ball and a proximal end of a gas cartridge.

8. The pen according to claim 1, wherein the applicator has a porosity of 10% to 95%.

9. The pen according to claim 8, wherein the porosity of the applicator has a variation of at most 30% with respect to the axial direction of the applicator.

10. The pen according to claim 9, wherein the porosity of the applicator is considered per transversal or perpendicular surface with respect to the axial direction.

11. The pen according to claim 1, further comprising a seal arranged at the distal end of the applicator holder, wherein the ball engages the seal in the rest position and thereby generates a sealed interface that prevents the coolant from flowing through the coolant passage to the applicator, and wherein the ball disengages the seal in the activated position and thereby allows the coolant to flow through the coolant passage to the applicator via the bypass.

12. The pen according to claim 1, wherein the distal end of the applicator holder comprises a concave seat that receives the ball, and wherein the bypass comprises a notch defined in the concave seat.

13. The pen according to claim 12, wherein the notch extends radially between an outer periphery of the distal end of the applicator holder and the coolant passage.

14. A pen for the treatment of dermatological disorders by means of a coolant, the pen comprising: a distal part comprising a holder for storage of the coolant; and a proximal part axially aligned with the distal part and comprising: an applicator for the administration of the coolant to a dermatological surface; and an applicator holder to which the applicator is mounted; a coolant passage extending axially through portions of the distal and proximal parts to communicate the coolant from the holder to the applicator; a ball biased against a distal end of the applicator holder and occluding the coolant passage when the pen is in a rest position and an activated position; and a bypass comprising a radially extending channel defined in the distal end of the applicator holder and in fluid communication with the coolant passage, wherein the coolant is prevented from flowing through the coolant passage to the applicator when the pen is in the rest position, wherein the coolant is allowed to flow through the coolant passage to the applicator via the bypass when the pen is moved to the activated position, wherein the applicator comprises a transformable foam, wherein said foam is a polyurethane foam with an average pore size of 400 μm to 700 μm.

15. The pen according to claim 14 further comprising a valve housing that houses the ball and at least the distal end of the applicator holder, wherein the holder is provided with a closed distal end and an open proximal end that receives a portion of the valve housing, and wherein a connecting mechanism secures the valve housing to the holder.

16. The pen according to claim 15, wherein the connecting mechanism includes at least one projecting part defined on the valve housing and that fits in a toothed pattern defined on the holder.

17. The pen according to claim 14, further comprising a removable closing cap positionable on the proximal part of the pen, the removable closing cap being provided with a ventilation opening for removing the coolant.

18. The pen according to claim 14, wherein the bypass does not extend axially.

19. The pen according to claim 14, wherein the diameter of the bypass is smaller than the diameter of the coolant passage.

20. The pen according to claim 14, wherein said foam has a hardness of 8 to 10 kPa.

21. The pen according to claim 14, wherein the applicator has a density of 19 to 67 kg/m3.

22. The pen according to claim 14, wherein said foam is polyester-polyurethane foam.

23. The pen according to claim 14, wherein the applicator comprises an administration surface, and the average pore size of the applicator decreases in the axial direction towards the administration surface.

24. The pen according to claim 23, wherein the average pore size of the applicator decreases from 60-250 μm to 0.1-55 μm.

25. The pen according to claim 14, wherein the proximal part of the pen further comprises a perforator located between the ball and a proximal end of a gas cartridge.

26. The pen according to claim 14 further comprising a removable closing cap for protecting the applicator,
   wherein said closing cap defines an inner volume with a decreasing diameter, and
   wherein the diameter decreases in a direction from the applicator holder towards an applicator tip or an administration surface.

* * * * *